(12) United States Patent
Ferrari et al.

(10) Patent No.: US 11,085,932 B2
(45) Date of Patent: Aug. 10, 2021

(54) PERIOSTIN FRAGMENTS AND USE THEREOF

(71) Applicant: UNIVERSITE DE GENEVE, Geneva (CH)

(72) Inventors: Serge Ferrari, Saconnex d'Arve/Genève (CH); Nicolas Bonnet, Cranves-Sales (FR); Daniel S. Spellman, West Point, PA (US)

(73) Assignee: UNIVERSITE DE GENEVE, Geneva (CH)

( * ) Notice: Subject to any disclaimer, the term of this patent is extended or adjusted under 35 U.S.C. 154(b) by 536 days.

(21) Appl. No.: 15/766,489

(22) PCT Filed: Oct. 7, 2016

(86) PCT No.: PCT/EP2016/074086
§ 371 (c)(1),
(2) Date: Apr. 6, 2018

(87) PCT Pub. No.: WO2017/060482
PCT Pub. Date: Apr. 13, 2017

(65) Prior Publication Data
US 2018/0284135 A1    Oct. 4, 2018

Related U.S. Application Data

(60) Provisional application No. 62/238,901, filed on Oct. 8, 2015.

(51) Int. Cl.
*G01N 33/68* (2006.01)
*C07K 16/18* (2006.01)
*C07K 14/475* (2006.01)

(52) U.S. Cl.
CPC ....... *G01N 33/6893* (2013.01); *C07K 14/475* (2013.01); *C07K 16/18* (2013.01); *G01N 2800/108* (2013.01); *G01N 2800/50* (2013.01); *G01N 2800/52* (2013.01)

(58) Field of Classification Search
None
See application file for complete search history.

(56) References Cited

U.S. PATENT DOCUMENTS

2003/0073137 A1*  4/2003  Chen .............. C07K 16/22
                                            435/7.5
2011/0033516 A1   2/2011  Markwald et al.

FOREIGN PATENT DOCUMENTS

WO    WO 2008/021290    2/2008

OTHER PUBLICATIONS

Helali, A. M. et al. "Cathepsin K Inhibitors: A Novel Target but Promising Approach in the Treatment of Osteoporosis" *Current Drug Targets*, 2013, pp. 1591-1600, vol. 14, No. 13.
(Continued)

*Primary Examiner* — Rebecca M Giere
(74) *Attorney, Agent, or Firm* — Saliwanchik, Lloyd & Eisenschenk

(57) ABSTRACT

The present invention relates to biological markers of metabolic bone diseases or disorders such as osteoporosis and related methods using thereof. The invention further relates to the use of those biomarkers and related material and assays in the diagnosis of subjects at risk of developing such disorders or monitoring the effects of a treatment thereof.

25 Claims, 8 Drawing Sheets
Specification includes a Sequence Listing.

(56) References Cited

OTHER PUBLICATIONS

Gineyts, E. et al. "The C-Terminal Intact Forms of Periostin (iPTN) Are Surrogate Markers for Osteolytic Lesions in Experimental Breast Cancer Bone Metastasis" *Calcified Tissue International*, Jun. 18, 2018, pp. 1-14.

Bonnet, N. "Increased Periostin in Cortical Bone of Cathepsin K Knock-Out Mice is Responsible for Higher Cortical Bone Mass and Strength" ASBMR Annual Meeting 2014, Poster Sessions, Presentation No. SU0172, Abstract Only, pp. 1-2.

Bonnet, N. et al. "Increased periostin in cortical bone of cathepsin K knock out mice is responsible for higher cortical bone mass and strength" ASBMR Annual Meeting 2014, Presentation No. SU0172, Poster, p. 1.

Anastasilakis, A.D. et al. "Circulating Periostin Levels do not Differ Between Postmenopausal Women with Normal and Low Bone Mass and are not Affected by Zoledronic Acid Treatment" *Home Metab Res*, 2014, pp. 145-149, vol. 46.

Bonnet, N. et al. "The Matricellular Protein Periostin Is Required for Sost, Inhibition and the Anabolic Response to Mechanical Loading and Physical Activity" *The Journal of Biological Chemistry*, Dec. 18, 2009, pp. 35939-35950, vol. 284, No. 51.

Bonnet, N. et al. "Periostin action in bone" *Molecular and Cellular Endocrinology*, 2016, pp. 75-82, vol. 432.

Bonnet, N. et al. "Cathepsin K Controls Cortical Bone Formation by Degrading Periostin" *Journal of Bone and Mineral Research*, 2017, pp. 1-10.

Bonnet, N. et al. "Serum Levels of a Cathepsin-K Generated Periostin Fragment Predict Incident Low-Trauma Fractures in Postmenopausal Women Independently of BMD and FRAX" *Journal of Bone and Mineral Research*, 2017, pp. 1-7.

Chapurlat, R. D. et al. "Novel biological markers of bone: from bone metabolism to bone physiology" *Rheumatology*, 2016, pp. 1714-1725, vol. 55.

Chevalley, T. et al. "Fracture history of healthy premenopausal women is associated with a reduction of cortical microstructural components at the distal radius" *Bone*, 2013, pp. 377-383, vol. 55.

Contié, S. et al. "Development of a New ELISA for Serum Periostin: Evaluation of Growth-Related Changes and Bisphosphonate Treatment in Mice" *Calcif Tissue Int*, Jun. 22, 2010, pp. 1-10.

Dodds, R. A. et al. "Human Osteoclast Cathepsin K Is Processed Intracellularly Prior to Attachment and Bone Resorption" *Journal of Bone and Mineral Research*, 2001, pp. 478-486, vol. 16, No. 3.

Duong, L.T. et al. "Cathepsin K Inhibition: A New Mechanism for the Treatment of Osteoporosis" *Calcif Tissue Int*, 2016, pp. 381-397, vol. 98.

Durosier, C. et al. "Association of Circulating Sclerostin With Bone Mineral Mass, Microstructure, and Turnover Biochemical Markers in Healthy Elderly Men and Women" *Journal of Clinical Endocrinology Metabolism*, Sep. 2013, pp. 3873-3883, vol. 98, No. 9.

Garnero, P. "New Developments in biological markers of bone metabolism in osteoporosis" *Bone*, 2014, pp. 46-55, vol. 66.

Garnero, P. et al. "Development of a New Immunoassay for Human Cathepsin K-Generated Periostin Fragments as a Serum Biomarker for Cortical Bone" *Calcif Tissue Int*, 2017, pp. 501-509, vol. 101.

Horiuchi, K. et al. "Identification and Characterization of a Novel Protein, Periostin, with Restricted Expression to Periosteum and Periodontal Ligament and Increased Expression by Transforming Growth Factor β" *Journal of Bone and Mineral Research*, 1999, pp. 1239-1249, vol. 14, No. 7.

Lippuner, K. et al. "FRAX® assessment of osteoporotic fracture probability in Switzerland" *Osteoporos Int*, 2010, pp. 381-389, vol. 21.

Meier, C. et al. "Serum Cathepsin K Concentrations Reflect Osteoclastic Activity in Women with Postmenopausal Osteoporosis and Patients with Paget's Disease" *Clin Lab*, 2006, pp. 1-10, vol. 52.

Merle, B. et al. "The multiple facets of periostin in bone metabolism" *Osteoporos Int*, 2012, pp. 1199-1212, vol. 23.

Shengyu, L. et al. "Histochemical examination of cathepsin K, MMP1 and MMP2 in compressed periodontal ligament during orthodontic tooth movement in periostin deficient mice" *J Mol Hist*, 2014, pp. 303-309, vol. 45.

Sun, S. et al. "The development and characterization of an ELISA specifically detecting the active form of cathepsin K" *Clinical Biochemistry*, 2013, pp. 1601-1606, vol. 46.

Written Opinion in International Application No. PCT/EP2016/074086, dated Jan. 10, 2017, pp. 1-7.

\* cited by examiner

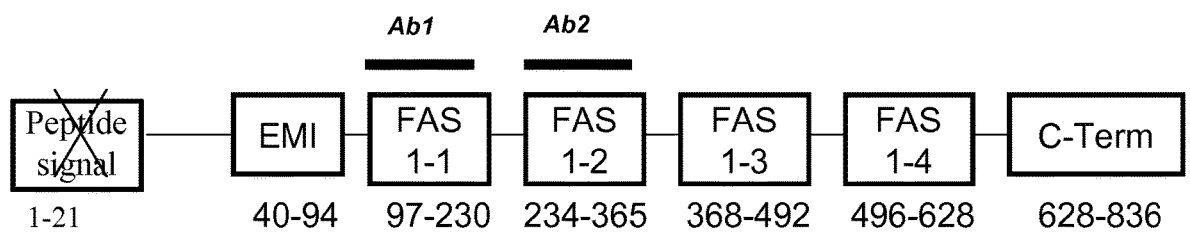
Figure 1
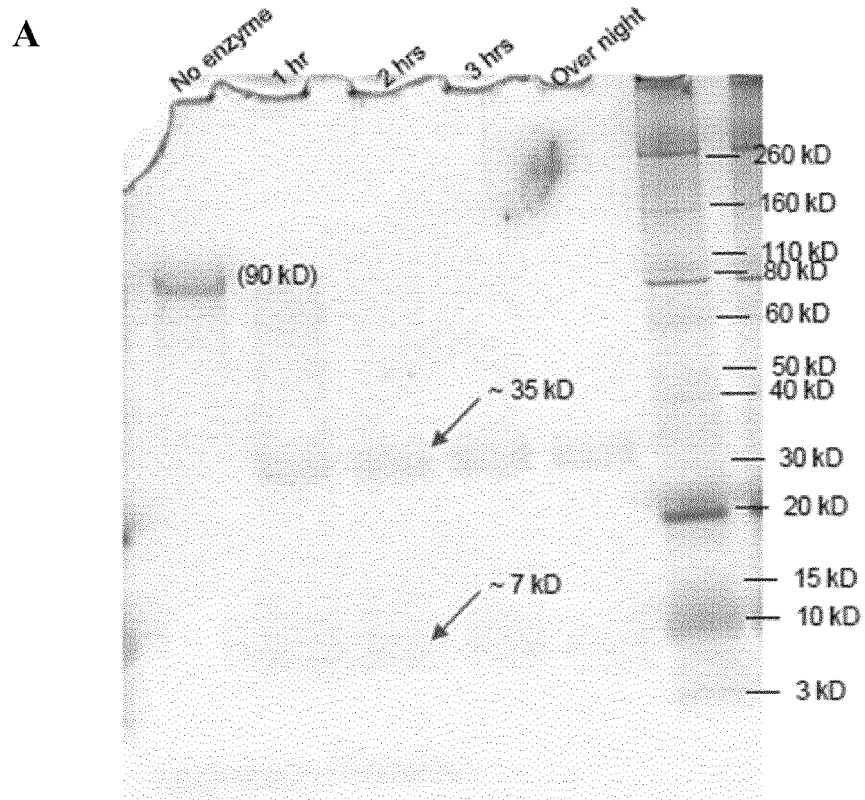
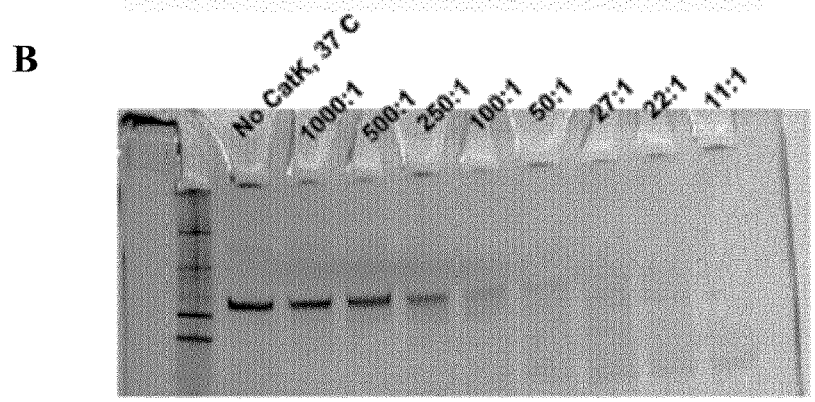
Figure 2

A

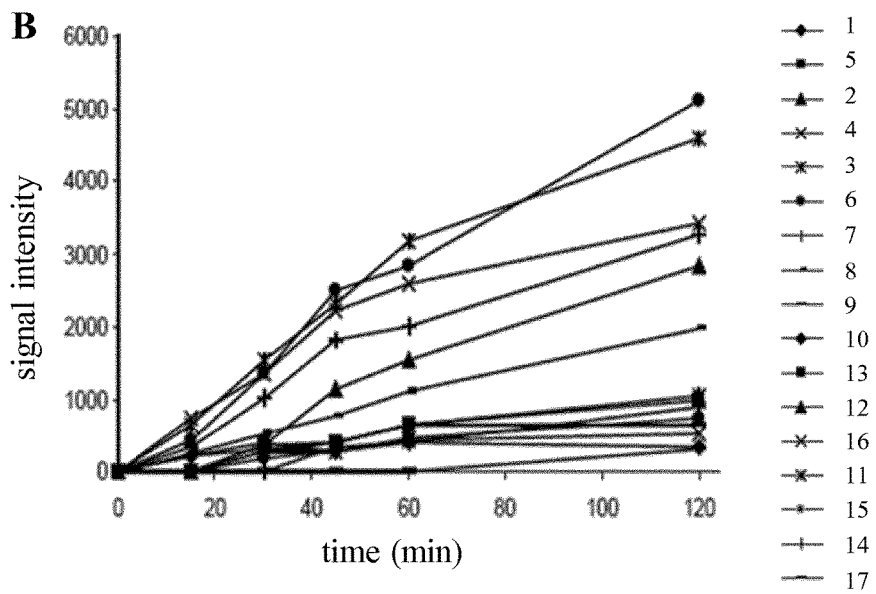

MIPFLPMFSLLLLLIVNPINANNHYDKILAHSRIRGRDQGPNVCALQQILGTKKKYFSTCKNWYKK
SICGQKTTVLYECCPGYMRMEGMKGCPAVLPIDHVYGTLGIVGATTTQRYSDASKLREEIEGKGSF
TYFAPSNEAWDNLDSDIRRGLESNVNVELLNALHSHMINKRMLTKDLKNGMIIPSMYNNLGLFINH
YPNGVVTVNCARIIHGNQIATNGVVHVIDRVLTQIGTSIQDFIEAEDDLSSFRAAAITSDILEALG
RDGHFTLFAPTNEAFEKLPRGVLERIMGDKVASEALMKYHILNTLQCSESIMGGAVFETLEGNTIE
IGCDGDSITVNGIKMVNKKDIVTNNGVIHLIDQVLIPDSAKQVIELAGKQQTTFTDLVAQLGLASA
LRPDGEYTLLAPVNNAFSDDTLSMDQRLLKLILQNHILKVKVGLNELYNGQILETIGGKQLRVFVY
RTAVCIENSCMEKGSKQGRNGAIHIFREIIKPAEKSLHEKLKQDKRFSTFLSLLEAADLKELLTQP
GDWTLFVPTNDAFKGMTSEEKEILIRDKNALQNIILYHLTPGVFIGKGFEPGVTNILKTTQGSKIF
LKEVNDTLLVNELKSKESDIMTTNGVIHVVDKLLYPADTPVGNDQLLEILNKLIKYIQIKFVRGST
FKEIPVTVYTTKIITKVVEPKIKVIEGSLQPIIKTEGPTLTKVKIEGEPEFRLIKEGETITEVIHG
EPIIKKYTKIIDGVPVEITEKETREERIITGPEIKYTRISTGGGETEETLKKLLQEEVTKVTKFIE
GGDGHLFEDEEIKRLLQGDTPVRKLQANKKVQGSRRRLREGRSQ

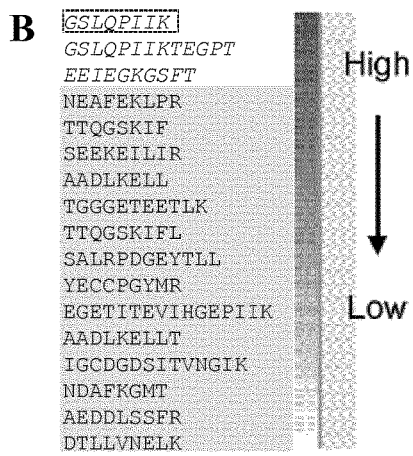

Figure 5

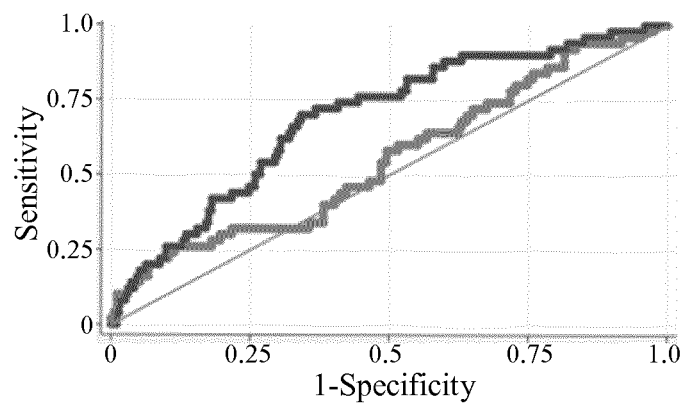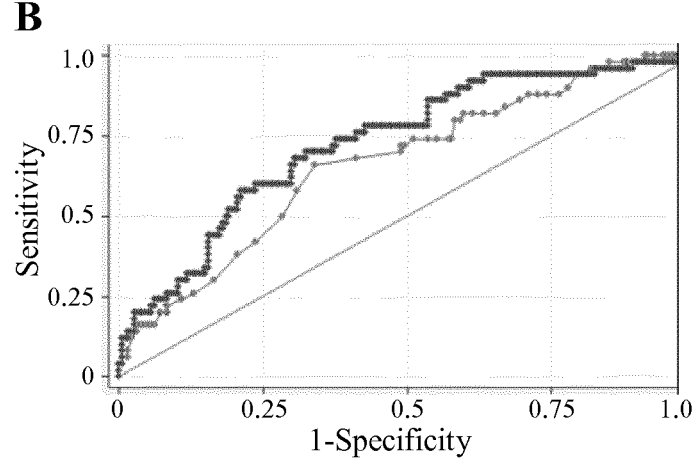
Figure 12

SEQUENCE LISTING

<160> NUMBER OF SEQ ID NOS: 25

<210> SEQ ID NO 1
<211> LENGTH: 836
<212> TYPE: PRT
<213> ORGANISM: Homo sapiens

<400> SEQUENCE: 1

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65              70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
290                 295                 300

Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
                325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
        355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp

```
            405                 410                 415
Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
            450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
            530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
            610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Thr Thr Lys
                660                 665                 670

Ile Ile Thr Lys Val Val Glu Pro Lys Ile Lys Val Ile Glu Gly Ser
            675                 680                 685

Leu Gln Pro Ile Ile Lys Thr Glu Gly Pro Thr Leu Thr Lys Val Lys
            690                 695                 700

Ile Glu Gly Glu Pro Glu Phe Arg Leu Ile Lys Glu Gly Glu Thr Ile
705                 710                 715                 720

Thr Glu Val Ile His Gly Glu Pro Ile Ile Lys Lys Tyr Thr Lys Ile
                725                 730                 735

Ile Asp Gly Val Pro Val Glu Ile Thr Glu Lys Glu Thr Arg Glu Glu
            740                 745                 750

Arg Ile Ile Thr Gly Pro Glu Ile Lys Tyr Thr Arg Ile Ser Thr Gly
            755                 760                 765

Gly Gly Glu Thr Glu Glu Thr Leu Lys Lys Leu Leu Gln Glu Glu Val
            770                 775                 780

Thr Lys Val Thr Lys Phe Ile Glu Gly Gly Asp Gly His Leu Phe Glu
785                 790                 795                 800

Asp Glu Glu Ile Lys Arg Leu Leu Gln Gly Asp Thr Pro Val Arg Lys
                805                 810                 815

Leu Gln Ala Asn Lys Lys Val Gln Gly Ser Arg Arg Leu Arg Glu
            820                 825                 830
```

Gly Arg Ser Gln
        835

<210> SEQ ID NO 2
<211> LENGTH: 8
<212> TYPE: PRT
<213> ORGANISM: Artificial Sequence
<220> FEATURE:
<223> OTHER INFORMATION: Periostin fragment 1

<400> SEQUENCE: 2

Gly Ser Leu Gln Pro Ile Ile Lys
1               5

<210> SEQ ID NO 3
<211> LENGTH: 10
<212> TYPE: PRT
<213> ORGANISM: Artificial Sequence
<220> FEATURE:
<223> OTHER INFORMATION: Periostin fragment 2

<400> SEQUENCE: 3

Glu Glu Ile Glu Gly Lys Gly Ser Phe Thr
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Periostin fragment 3

<400> SEQUENCE: 4

Thr Thr Gln Gly Ser Lys Ile Phe
1               5

<210> SEQ ID NO 5
<211> LENGTH: 9
<212> TYPE: PRT
<213> ORGANISM: Artificial Sequence
<220> FEATURE:
<223> OTHER INFORMATION: Periostin fragment 4

<400> SEQUENCE: 5

Asn Glu Ala Phe Glu Lys Leu Pro Arg
1               5

<210> SEQ ID NO 6
<211> LENGTH: 13
<212> TYPE: PRT
<213> ORGANISM: Artificial Sequence
<220> FEATURE:
<223> OTHER INFORMATION: Periostin fragment 5

<400> SEQUENCE: 6

Gly Ser Leu Gln Pro Ile Ile Lys Thr Glu Gly Pro Thr
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Periostin fragment 6

<400> SEQUENCE: 7

```
Ser Glu Glu Lys Glu Ile Leu Ile Arg
1               5
```

<210> SEQ ID NO 8
<211> LENGTH: 8
<212> TYPE: PRT
<213> ORGANISM: Artificial Sequence
<220> FEATURE:
<223> OTHER INFORMATION: Periostin fragment 7

<400> SEQUENCE: 8

```
Ala Ala Asp Leu Lys Glu Leu Leu
1               5
```

<210> SEQ ID NO 9
<211> LENGTH: 11
<212> TYPE: PRT
<213> ORGANISM: Artificial Sequence
<220> FEATURE:
<223> OTHER INFORMATION: Periostin fragment 8

<400> SEQUENCE: 9

```
Thr Gly Gly Gly Glu Thr Glu Glu Thr Leu Lys
1               5                   10
```

<210> SEQ ID NO 10
<211> LENGTH: 9
<212> TYPE: PRT
<213> ORGANISM: Artificial Sequence
<220> FEATURE:
<223> OTHER INFORMATION: Periostin fragment 9

<400> SEQUENCE: 10

```
Thr Thr Gln Gly Ser Lys Ile Phe Leu
1               5
```

<210> SEQ ID NO 11
<211> LENGTH: 12
<212> TYPE: PRT
<213> ORGANISM: Artificial Sequence
<220> FEATURE:
<223> OTHER INFORMATION: Periostin fragment 10

<400> SEQUENCE: 11

```
Ser Ala Leu Arg Pro Asp Gly Glu Tyr Thr Leu Leu
1               5                   10
```

<210> SEQ ID NO 12
<211> LENGTH: 16
<212> TYPE: PRT
<213> ORGANISM: Artificial Sequence
<220> FEATURE:
<223> OTHER INFORMATION: Periostin fragment 11

<400> SEQUENCE: 12

```
Glu Gly Glu Thr Ile Thr Glu Val Ile His Gly Glu Pro Ile Ile Lys
1               5                   10                  15
```

<210> SEQ ID NO 13
<211> LENGTH: 9
<212> TYPE: PRT
<213> ORGANISM: Artificial Sequence
<220> FEATURE:
<223> OTHER INFORMATION: Periostin fragment 12

<400> SEQUENCE: 13

```
Tyr Glu Cys Cys Pro Gly Tyr Met Arg
```

```
<210> SEQ ID NO 14
<211> LENGTH: 9
<212> TYPE: PRT
<213> ORGANISM: Artificial Sequence
<220> FEATURE:
<223> OTHER INFORMATION: Periostin fragment 13

<400> SEQUENCE: 14

Ala Ala Asp Leu Lys Glu Leu Leu Thr
1               5

<210> SEQ ID NO 15
<211> LENGTH: 14
<212> TYPE: PRT
<213> ORGANISM: Artificial Sequence
<220> FEATURE:
<223> OTHER INFORMATION: Periostin fragment 14

<400> SEQUENCE: 15

Ile Gly Cys Asp Gly Asp Ser Ile Thr Val Asn Gly Ile Lys
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Periostin fragment 15

<400> SEQUENCE: 16

Asn Asp Ala Phe Lys Gly Met Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Periostin fragment 16

<400> SEQUENCE: 17

Ala Glu Asp Asp Leu Ser Ser Phe Arg
1               5

<210> SEQ ID NO 18
<211> LENGTH: 9
<212> TYPE: PRT
<213> ORGANISM: Artificial Sequence
<220> FEATURE:
<223> OTHER INFORMATION: Periostin fragment 17

<400> SEQUENCE: 18

Asp Thr Leu Leu Val Asn Glu Leu Lys
1               5

<210> SEQ ID NO 19
<211> LENGTH: 329
<212> TYPE: PRT
<213> ORGANISM: Artificial Sequence
<220> FEATURE:
<223> OTHER INFORMATION: Homo sapiens CatK

<400> SEQUENCE: 19

Met Trp Gly Leu Lys Val Leu Leu Leu Pro Val Val Ser Phe Ala Leu
1               5                   10                  15
```

```
Tyr Pro Glu Glu Ile Leu Asp Thr His Trp Glu Leu Trp Lys Lys Thr
             20                  25                  30

His Arg Lys Gln Tyr Asn Asn Lys Val Asp Glu Ile Ser Arg Arg Leu
         35                  40                  45

Ile Trp Glu Lys Asn Leu Lys Tyr Ile Ser Ile His Asn Leu Glu Ala
 50                  55                  60

Ser Leu Gly Val His Thr Tyr Glu Leu Ala Met Asn His Leu Gly Asp
 65                  70                  75                  80

Met Thr Ser Glu Glu Val Val Gln Lys Met Thr Gly Leu Lys Val Pro
                 85                  90                  95

Leu Ser His Ser Arg Ser Asn Asp Thr Leu Tyr Ile Pro Glu Trp Glu
             100                 105                 110

Gly Arg Ala Pro Asp Ser Val Asp Tyr Arg Lys Lys Gly Tyr Val Thr
         115                 120                 125

Pro Val Lys Asn Gln Gly Gln Cys Gly Ser Cys Trp Ala Phe Ser Ser
130                 135                 140

Val Gly Ala Leu Glu Gly Gln Leu Lys Lys Lys Thr Gly Lys Leu Leu
145                 150                 155                 160

Asn Leu Ser Pro Gln Asn Leu Val Asp Cys Val Ser Glu Asn Asp Gly
                 165                 170                 175

Cys Gly Gly Gly Tyr Met Thr Asn Ala Phe Gln Tyr Val Gln Lys Asn
             180                 185                 190

Arg Gly Ile Asp Ser Glu Asp Ala Tyr Pro Tyr Val Gly Gln Glu Glu
         195                 200                 205

Ser Cys Met Tyr Asn Pro Thr Gly Lys Ala Ala Lys Cys Arg Gly Tyr
210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
             245                 250                 255

Gln Phe Tyr Ser Lys Gly Val Tyr Tyr Asp Glu Ser Cys Asn Ser Asp
         260                 265                 270

Asn Leu Asn His Ala Val Leu Ala Val Gly Tyr Gly Ile Gln Lys Gly
             275                 280                 285

Asn Lys His Trp Ile Ile Lys Asn Ser Trp Gly Glu Asn Trp Gly Asn
         290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                325

<210> SEQ ID NO 20
<211> LENGTH: 9
<212> TYPE: PRT
<213> ORGANISM: Artificial Sequence
<220> FEATURE:
<223> OTHER INFORMATION: Control Peptide 1

<400> SEQUENCE: 20

Gly Ser Leu Gln Pro Ile Ile Lys Thr
1               5

<210> SEQ ID NO 21
<211> LENGTH: 7
<212> TYPE: PRT
<213> ORGANISM: Artificial Sequence
```

```
<220> FEATURE:
<223> OTHER INFORMATION: Control Peptide 2

<400> SEQUENCE: 21

Gly Ser Leu Gln Pro Ile Ile
1               5

<210> SEQ ID NO 22
<211> LENGTH: 13
<212> TYPE: PRT
<213> ORGANISM: Artificial Sequence
<220> FEATURE:
<223> OTHER INFORMATION: Periostin fragment 18

<400> SEQUENCE: 22

Thr Asn Gly Val Val His Val Ile Asp Arg Val Leu Thr
1               5                   10

<210> SEQ ID NO 23
<211> LENGTH: 17
<212> TYPE: PRT
<213> ORGANISM: Artificial Sequence
<220> FEATURE:
<223> OTHER INFORMATION: Periostin fragment 19

<400> SEQUENCE: 23

Thr Ser Ile Gln Asp Phe Ile Glu Ala Glu Asp Leu Ser Ser Phe
1               5                   10                  15

Arg

<210> SEQ ID NO 24
<211> LENGTH: 14
<212> TYPE: PRT
<213> ORGANISM: Artificial Sequence
<220> FEATURE:
<223> OTHER INFORMATION: Periostin fragment 20

<400> SEQUENCE: 24

Ala Thr Thr Thr Gln Arg Tyr Ser Asp Ala Ser Lys Leu Arg
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Periostin fragment 21

<400> SEQUENCE: 25

Ala Pro Thr Asn Glu Ala Phe Glu Lys Leu Pro Arg
1               5                   10
```

PERIOSTIN FRAGMENTS AND USE THEREOF

CROSS-REFERENCE TO RELATED APPLICATIONS

This application is the U.S. national stage application of International Patent Application No. PCT/EP2016/074086, filed Oct. 7, 2016, which claims the benefit of U.S. Provisional Patent Application No. 62/238,901, filed Oct. 8, 2015.

The Sequence Listing for this application is labeled "Seq-List.txt" which was created on Mar. 23, 2018 and is 15 KB. The entire content of the sequence listing is incorporated herein by reference in its entirety.

FIELD OF THE INVENTION

The present invention relates generally to the field of biological markers and in particular biological markers of metabolic bone diseases such as osteoporosis. In particular, the invention relates to methods useful for the treatment and diagnosis of patients at risk of osteoporosis and monitoring progression of treatment thereof.

BACKGROUND OF THE INVENTION

The periosteum covers long bones and plays an important role in controlling the bone diameter and bone strength, however non-invasive methods of assessment of periosteal metabolism are not yet developed (Contié et al., 2010, *Calcif. Tissue Int.*, 87(4): 341-50; Garnero, 2014, *Bone*, 66: 46-55). Periostin (POSTN) is a 90-KDa matricellular gamma-carboxyglutamic acid protein preferentially expressed in periosteum and bone mesenchymal stem cells but also in collagen rich tissues subjected to mechanical strain, such as periodontal ligaments, heart valves, tendons and skin (Contié et al., 2010, supra; Merle et al., 2012, *Osteoporos. Int.*, 23: 1199-212). Periostin, initially known also as osteoblast-specific factor-2, is an 811-amino acid protein comprising an N-terminal secretory signal peptide, followed by an Emilin (EMI) cysteine rich domain, four internal homologous repeats so called Fasciclin-1 (FAS-1) domains, and a C-terminal hydrophilic and variable domain (Merle et al., 2012, supra). Periostin is an important regulator of osteoblastic activity, bone formation and regulation of bone strength by regulating collagen crosslinking, particularly at cortical sites and also osteoclastic activity by increasing Osteoprotegerin but it is not specific to bone tissue. POSTN exists in different forms due to alternative splicing (7 isoforms), gamma-carboxylation and dimerization, currently it is not known if one of the isoforms could be specific only for bone tissue (Merle et al., 2012, supra). Some data on the function of POSTN in bone metabolism have been obtained from the examination of POSTN deficient mice (Bonnet et al., 2009, *J. Biol. Chem.*, 284: 35939-50). These mice develop periodontis and osteoporosis with lower bone mineral density (BMD), altered microarchitecture and decreased bone strength. This study has also shown that POSTN is an important mediator of the effects of mechanical factors and parathyroid hormone on cortical BMD and bone strength by modulating the canonical wnt signaling pathway with a down regulation of sclerostin expression (Bonnet et al., 2009, supra). POSTN is secreted by osteocytes, osteoblasts and to low extend by osteoclasts and has been proposed to be a potential bone marker of cortical structure parameters (Garnero, 2014, supra). Because POSTN is a secreted protein it can be detected e.g. in peripheral blood and thus POSTN immunoassays have been developed for rodents (Contié et al., 2010, supra) and humans (Anastasilakis et al., 2014, *Horm. Metab. Res.*, 46: 145-9). However, these assays detect serum POSTN levels independent of their origin or isoform type and thus are non-specific. Various antibodies have been developed targeting different POSTN epitopes as represented on FIG. 1: polyclonal antibodies to human POSTN (Uscn Life Science, Inc.; Product No.: SEH339Hu) target the region of amino acids 97-230 (FAS 1-1) and monoclonal antibodies to human and mouse POSTN (Adipogen AG.; Product No.: BI-20433) target the region of amino acids 234-365 (FAS 1-2). However, those antibodies do not recognize a specific isoform of POSTN nor a tissue specific fragment. Among identified biochemical markers of bone metabolism, CTX (cross-linked C-terminal telopeptide of type I collagen) is used as a marker of bone resorption and P1NP (procollagen type 1 N-terminal propeptide) is used as a marker of bone remodelling. However, those markers are not specific of the trabecular/cortical compartments. Therefore, there is a need to identify markers and develop assays directed to assessment of metabolism of cortical bone that are more specific than detection of overall serum POSTN levels. Further, there are currently no anabolic agents able to increase trabecular bone formation except parathyroid hormone (PTH) which is known for having severe side effects. Therefore, there is a need to develop tools for the monitoring of the trabecular/cortical compartments in view of the identification of alternative anabolic agents.

Cathepsin K (CatK) is an enzyme, specifically a protease, which is defined by its high specificity for kinins and is involved in bone metabolism. It is a lysosomal enzyme synthesized as a procathepsin K, which is activated in the lysosomes through a process involving autocatalytic cleavage at low pH, and then released into the resorption lacunae (Dodds et al., 2001, *J. Bone Miner. Res.*, 16: 478-86). Cathepsin K is one of the main catalytic enzymes expressed and secreted by the osteoclasts. It is critical in osteoclast-mediated bone resorption as it plays a predominant role in the degradation of bone type I collagen (Garnero, 2014, supra). Consequently CatK metabolic pathway became a drug target in treatment of osteoporosis, e.g. CatK inhibitors, such as odanacatib have been developed (Helali et al., 2013, *Curr. Drug Targets*, 14: 1591-600).

Independently, some of CatK can be further released in the circulation and thus it was speculated to be a biological marker of osteoclast activity. Several assays for detection of CatK from blood have been developed, although it remains unclear whether they detect the proenzyme, the active form or both (Garnero, 2014, supra). By using such tests, it has been shown that serum CatK is increased in patients with osteoporosis (Meier et al., 2006, *Clin. Lab*, 52: 1-10). Further, by using an assay directed to detecting only the active form of CatK, no change in serum of active cathepsin K levels could be observed in postmenopausal women treated with anti-resorptive therapy (Sun et al., 2013, *Clin. Biochem.*, 46: 1606-6). Cathepsin K inhibitors are currently developed for the treatment of osteoporosis and other skeletal disorders associated with excessive bone remodeling (Odanacatib, Merck & Co., Inc.) but the currently available biomarkers do not offer an appropriate tool to monitor the effects of those inhibitors on the remodeling activity in the trabecular/cortical compartments.

Therefore, it is currently of interest to develop assays that measure specific markers of cathepsin K activity in relation to bone cortical structure in order to monitor pathophysiological metabolism of bone in patients with bone disorders

SUMMARY OF THE INVENTION

The present invention is based on the unexpected finding that POSTN is a substrate for CatK-mediated degradation that is restricted to bones, specifically to bone cortical region. CatK-dependent cleavage products (POSTN fragments) could therefore serve as biomarkers of bone metabolic changes related to bone disorders such as osteoporosis.

In particular, it has been identified POSTN fragments which are specific of the bone tissue as opposed to intact POSTN. More particularly, the invention is based on the finding of markers of the bone quality, in particular in term of the cortical microstructure and bone matrix, which markers can be used as reliable predictive indicators of the risk of fracture in a subject. The present invention is directed towards a method of detection of POSTN fragments from a biological fluid sample of a mammalian subject and related antibodies, assay and kits suitable for the diagnosis of patients at risk of developing a metabolic bone disorder such as osteoporosis and monitoring the effect of a treatment thereof.

One aspect of the invention provides an isolated peptide POSTN fragment or variants thereof.

Another aspect of the invention relates to an isolated peptide POSTN fragment or variants thereof, or formulation thereof according to the invention for use in the prevention and/or treatment of a metabolic bone disorder such as osteoporosis.

Another aspect of the invention provides a process of producing POSTN fragments or variants thereof comprising incubating POSTN with CatK.

Other aspect of the invention relates to an isolated nucleic acid molecule encoding a POSTN fragment or variant thereof as described herewith.

Another aspect of the invention relates to an isolated antibody or fragment thereof specific for POSTN fragment or variant thereof.

Another aspect of the invention relates to an isolated nucleic acid molecule encoding an antibody or fragment thereof as described herewith.

Another aspect of the invention relates to a recombinant expression vector comprising said nucleic acid molecule, and to a host cell comprising said recombinant vector, respectively.

Another aspect of the invention relates to a process for producing antibodies or fragments thereof as described herewith comprising culturing a host cell transformed with an expression vector comprising a nucleic acid sequence that encodes said antibodies or fragments thereof under conditions sufficient to promote expression of said antibodies or fragments thereof.

Next aspect of the invention provides a method for detecting a POSTN fragment from a biological fluid sample of a mammalian subject comprising the steps of:
(a) providing a biological fluid sample obtained from a mammalian subject;
(b) bringing said biological fluid sample into contact with a solid matrix where at least one antibody is bound to, wherein the contacting is under conditions sufficient for binding a POSTN fragment of the invention present in said biological fluid sample to said at least one antibody through antigen-antibody interactions and wherein said at least one antibody is specific for POSTN fragment of the invention or any variant thereof;
(c) removing the biological fluid sample from the solid matrix for removing any unbound POSTN fragment of the invention from the surface of the said solid matrix;
(d) detecting the presence of an antigen-antibody complex bound to the said solid matrix, wherein the presence of the said complex is indicative that the biological fluid sample contains one or more POSTN fragments of the invention.

Next aspect of the invention provides a method for detecting a POSTN fragment from a biological fluid sample of a mammalian subject comprising the steps of:
(a) providing a biological fluid sample obtained from a mammalian subject;
(b) bringing said biological fluid sample into contact with at least one antibody, wherein the contacting is under conditions sufficient for binding a POSTN fragment of the invention present in said biological fluid sample to said at least one antibody through antigen-antibody interactions and wherein said at least one antibody is specific for POSTN fragment of the invention or any variant thereof;
(c) bringing sample obtained under step b) into contact with a solid matrix where at least one POSTN fragment of the invention is bound to, wherein the contacting is under conditions sufficient for binding an antibody specific for POSTN fragment of the invention present in said sample to said at least one POSTN fragment of the invention through antigen-antibody interactions;
(d) washing the solid matrix for removing any unbound antibody from the surface of the said solid matrix;
(e) detecting the presence of an antigen-antibody complex bound to the said solid matrix, wherein the presence of the said complex is indicative that the biological fluid sample contains one or more POSTN fragments of the invention.

In another aspect, the invention provides a method for detecting a POSTN fragment from a biological fluid sample of a mammalian subject comprising the steps of:
(a) providing a biological fluid sample obtained from a mammalian subject;
(b) providing a solid support having bound thereto at least one POSTN fragments of the invention;
(c) bringing said solid support into contact with said biological fluid sample;
(d) bringing said solid support into contact with at least one antibody specific for POSTN fragment of the invention or any variant thereof, wherein the contacting is under conditions sufficient for binding a POSTN fragment of the invention present in said biological fluid sample to said at least one antibody through antigen-antibody interactions;
(e) washing the solid matrix for removing any unbound antibody from the surface of the said solid matrix;
(f) detecting the presence of an antigen-antibody complex bound to the said solid matrix, wherein the presence of the said complex is indicative that the biological fluid sample contains one or more POSTN fragments of the invention.

In another aspect, the invention provides an immunoassay preparation for the detection of a POSTN fragment of the invention comprising at least one antibody according to the invention.

Another aspect of the invention relates a kit for detecting a POSTN fragment of the invention in a biological fluid sample, the kit comprising at least one antibody according to the invention or a variant thereof.

Another aspect of the invention provides a method of monitoring the effects of a treatment of metabolic bone disorders, comprising detection of a POSTN fragment of the invention in a biological fluid sample from a subject under treatment.

Another aspect of the invention provides a method of diagnosis of subjects at risk of developing a metabolic bone disorder such as osteoporosis comprising detection of a POSTN fragment of the invention.

Another aspect of the invention provides an indirect method of evaluating cortical bone volume and porosity comprising detection of a POSTN fragment of the invention.

DESCRIPTION OF THE FIGURES

FIG. 1 is schematic representation of the amino acid sequence of POSTN with its different domains: the EMI domain, the four FAS domains and the C terminal (C-Term) variable region. Numbers indicate amino acid positions on the mature POSTN amino acid sequence. The peptide signal at N terminal is indicated as cleaved. Ab1: commercial antibodies to human POSTN (USCN) targeting 97-230 (FAS 1-1), Ab2: commercial antibodies to human and mouse POSTN (Adipogen AG) targeting 234-365 (FAS 1-2).

FIG. 2 shows SDS-PAGE gel of CatK digested human POSTN (A-B). A: Digestion lasting for 1 h, 2 h, 3 h or overnight with constant POSTN/CatK ratio of 50:1 as described in Example 1. Molecular weight (MW) in kDa of peptides is indicated. B: Digestion of constant amount of POSTN for 4 h, at 37°, with increasing amount of CatK; POSTN/CatK ratios ranging from 1000:1 to 11:1 are indicated. A-B: POSTN fragments were visualized by silver staining; dominant band at around 90 kDa corresponds to POSTN.

FIG. 5 shows an overview of CatK-cleavage POSTN fragments sites in human POSTN (A) (SEQ ID NO: 1) and their abundance as measured by LC-MS/MS (B) (SEQ ID NOs: 2, 6, 3, 5, 4, 7-11, 13, 12 and 14-18, respectively).

FIG. 12 shows ROC curves comparison for A: BMD femoral neck (AUC=0.555; grey) versus BMD femoral neck and peptide 1 (AUC=0.692; black) p=0.005; B: FRAX (AUC=0.667; grey) versus FRAX and peptide 1 (AUC=0.730; black) as described in Example 12.

DETAILED DESCRIPTION

Figure 3:
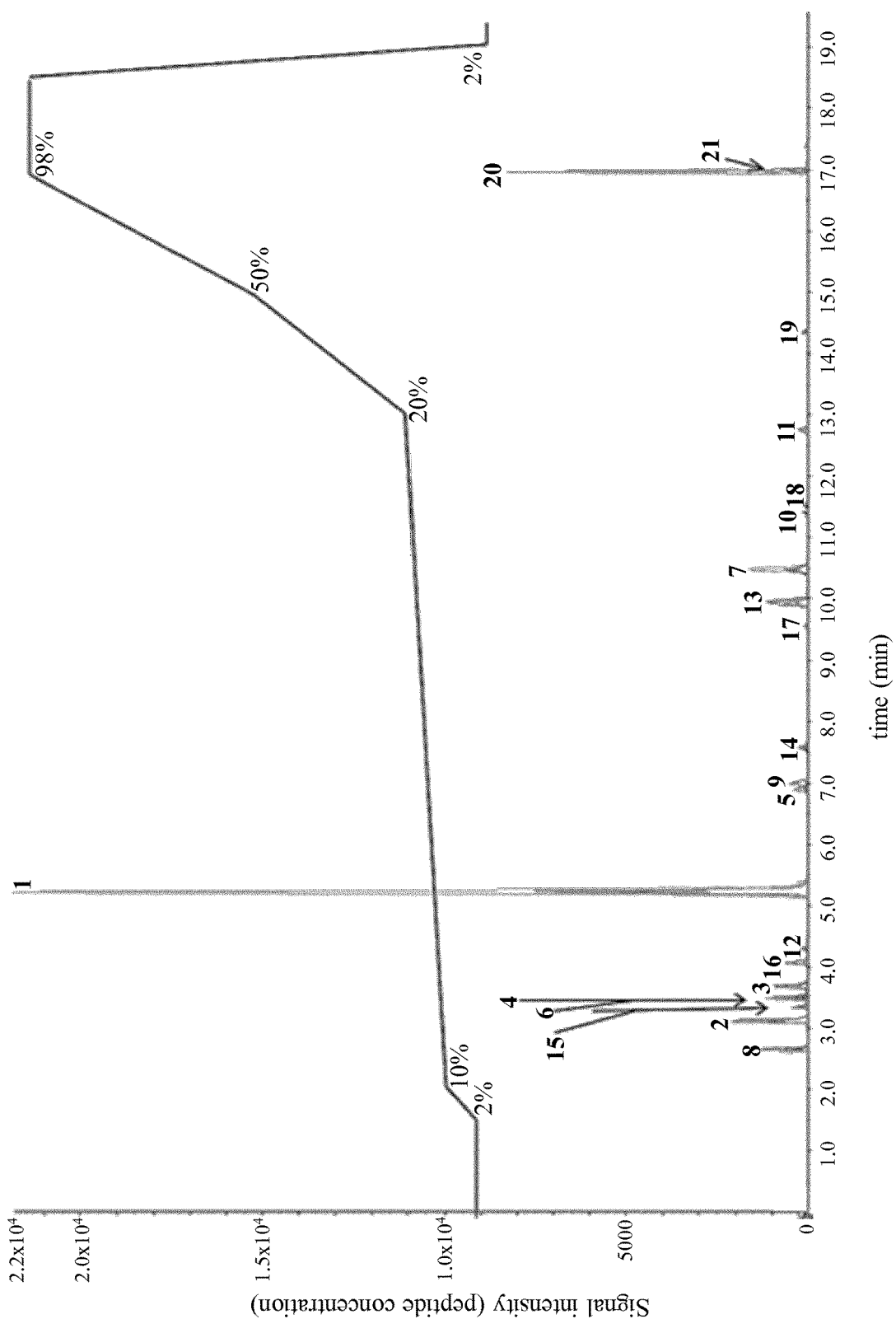
FIG. 3 shows twenty-one different POSTN fragments separated in a single LC-MS/MS analysis as described in Example 2. A: The sequences of the identified POSTN fragments are indicated on the corresponding signal. The relative % absorbance is indicated. B: LC-MS/MS measurement of the two major CatK-cleavage POSTN fragments obtained with POSTN/CatK ratio ranging from 250:1 to 5:1. 1- Peptide 1 (SEQ ID NO: 2), 2- Peptide 2 (SEQ ID NO: 3), 3- Peptide 3 (SEQ ID NO: 4), 4- Peptide 4 (SEQ ID NO: 5), 5- Peptide 5 (SEQ ID NO: 6), 6- Peptide 6 (SEQ ID NO: 7), 7- Peptide 7 (SEQ ID NO: 8), 8- Peptide 8 (SEQ ID NO: 9), 9- Peptide 9 (SEQ ID NO: 10), 10- Peptide 10 (SEQ ID NO: 11), 11- Peptide 11 (SEQ ID NO: 12), 12- Peptide 12 (SEQ ID NO: 13), 13- Peptide 13 (SEQ ID NO: 14), 14- Peptide 14 (SEQ ID NO: 15), 15- Peptide 15 (SEQ ID NO: 16), 16- Peptide 16 (SEQ ID NO: 17), 17- Peptide 17 (SEQ ID NO: 18), 18- Peptide 18 (SEQ ID NO: 22), 19- Peptide 19 (SEQ ID NO: 23), 20- Peptide 20 (SEQ ID NO: 24), 21- Peptide 21 (SEQ ID NO: 25).
Figure 3:
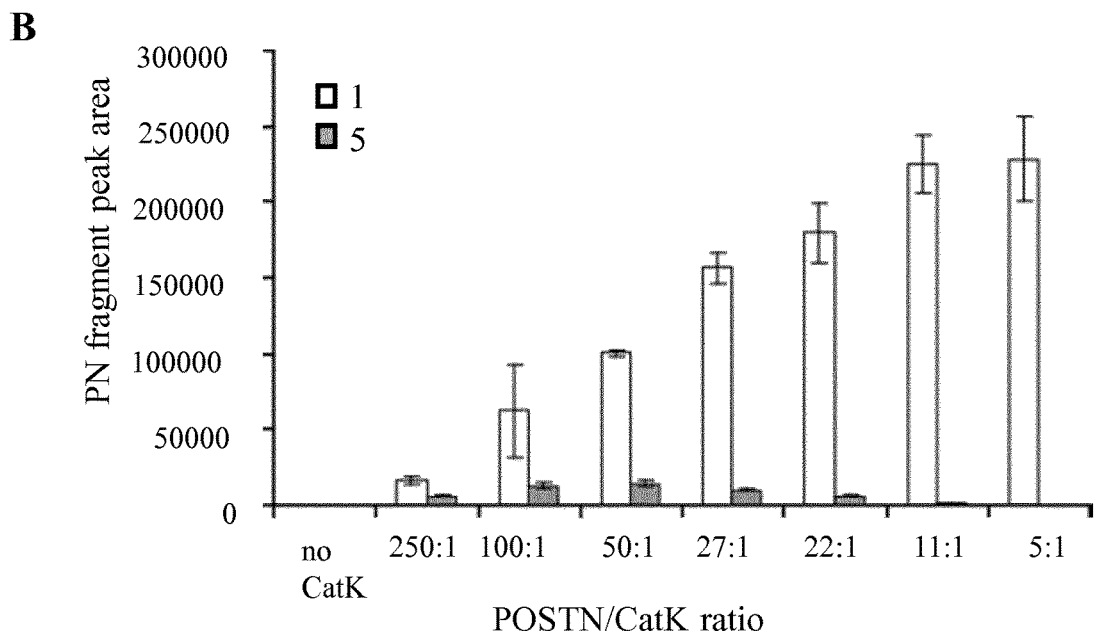

"Polypeptide" is understood as a peptide, an oligopeptide, an oligomer or a protein comprising at least two amino acids joined to each other by a normal or modified peptide bond, such as in the cases of the isosteric peptides, for example. A polypeptide can be composed of amino acids other than the 20 amino acids defined by the genetic code. A polypeptide can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the lateral chain or even at the carboxy- or amino-terminal ends. For example, polypeptide modifications are understood to include phosphorylations, glycolysation, isomerisation, gamma carboxylation, dimerisation. Such modifications are fully detailed in the literature (*Proteins Structure and Molecular Properties* (1993) 2$^{nd}$ Ed., T. E. Creighton, New York; *Post-translational Covalent Modifications of Proteins* (1983) B. C. Johnson, Ed., Academic Press, New York; Seifter et al. (1990) *Analysis for protein modifications and nonprotein cofactors, Meth. Enzymol.* 182: 626-646 and Rattan et al., (1992) *Protein Synthesis: Post-translational Modifications and Aging, Ann NY Acad Sci*, 663: 48-62).

The term "periostin", abbreviated "POSTN", also known as osteoblast-specific factor-2, is a matricellular gamma-carboxyglutamic acid polypeptide protein preferentially expressed in periosteum and bone mesenchymal stem cells. POSTN can also be expressed in collagen rich tissues subjected to mechanical strain such as periodontal ligaments, heart valves and tendons. POSTN is an 811-amino acid protein of SEQ ID NO: 1, comprising an N-terminal secretory signal peptide, followed by an Emilin (EMI) cysteine rich domain, four internal homologous repeats so called Fasciclin-1 (FAS-1) domains, and a C-terminal hydrophilic domain and variable domain. The recombinant human POSTN (Horiuchi et al., 1999, *J Bone Miner Res* 14:1239) comprises an N-terminal secretory signal peptide (residues 1-21 from SEQ ID NO: 1) that is not present in mature form of POSTN, EMI domain (residues 40-94 from SEQ ID NO: 1), 4 of FAS-1 domains (respectively residues 97-230, 234-365, 368-492 and 496-628 from SEQ ID NO:

1) and C-terminal variable domain (residues 628-836 from SEQ ID NO: 1), FIG. 1. The term "periostin fragment" or "POSTN fragment" refers to a polypeptide POSTN fragment according to the invention obtained after CatK-dependent degradation in bone.

The term "cathepsin K", abbreviated "CatK", as referred to herein, means an enzyme of reference EC:3.4.22.38, specifically a protease, which is defined by its high specificity for kinins and is involved in bone resorption. CatK catabolizes elastin, collagen, and gelatin and allows it to break down bone and cartilage. CatK is highly and selectively expressed by osteoclast and is critical in osteoclast-mediated bone resorption. An example sequence of human CatK is provided as SEQ ID NO: 19.

The term "isolated" is used to indicate that the molecule is free of association with other proteins or polypeptides, for example as a purification product. Further, "isolated peptide" or "isolated polypeptide" is understood as a polypeptide such as POSTN fragment which is isolated from the human body or otherwise produced by a technical process.

The term "variant" as referred to herein, means a polypeptide substantially homologous to the original peptide sequence, but which has at least one an amino acid sequence different from that of the original sequence because of one or more deletions, insertions or substitutions. Substantially homologous means a variant amino acid sequence that is at least 80%, at least 85%, at least 90%, at least 95%, at least 96%, at least 97%, at least 98% or at least 99% identical to the original amino acid sequences, as disclosed above. The percentage identity of two amino acid sequences can be determined by visual inspection and/or mathematical calculation, or more easily by comparing sequence information using known computer program used for sequence comparison such as Clustal package version 1.83. A variant may comprise a sequence having at least one conservatively substituted amino acid, meaning that a given amino acid residue is replaced by a residue having similar physiochemical characteristics. Generally, substitutions for one or more amino acids present in the original polypeptide should be made conservatively. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known (Kyte, et al, 1982, *J. Mol. Biol.,* 157: 105-131). For example, a "conservative amino acid substitution" may involve a substitution of a native amino acid residue with a non-native residue such that there is little or no effect on the polarity or charge of the amino acid residue at that position. Desired amino acid substitutions (whether conservative or non-conservative) can be determined by those skilled in the art at the time such substitutions are desired. Exemplary amino acid substitutions are presented in Table 1 below:

TABLE 1

| Original residues | Examples of substitutions |
|---|---|
| Ala (A) | Val, Leu, Ile |
| Arg (R) | Lys, Gln, Asn |
| Asn (N) | Gln |
| Asp (D) | Glu |
| Cys (C) | Ser, Ala |
| Gln (Q) | Asn |
| Glu (E) | Asp |
| Gly (G) | Pro, Ala |
| His (H) | Asn, Gln, Lys, Arg |
| Ile (I) | Leu, Val, Met, Ala, Phe, Norleucine |
| Leu (L) | Ile, Val, Met, Ala, Phe, Norleucine |
| Lys (K) | Arg, Gln, Asn |
| Met (M) | Leu, Ile, Phe |
| Phe (F) | Leu, Val, Ile, Ala, Tyr |
| Pro (P) | Ala, Gly |
| Ser (S) | Thr, Ala, Cys |
| Thr (T) | Ser |
| Tyr (Y) | Trp, Phe, Thr, Ser |
| Val (V) | Ile Met, Leu, Phe, Ala, Norleucine |

The expression "biological fluid sample" refers to a clinical fluid sample for testing which is taken from a body fluid from a mammal such as saliva, bone marrow, blood, pleural liquid, sweat and urine. For example, a biological fluid sample is a serum/plasma sample from a human subject.

The expression "control sample" refers to a positive control or a negative control sample. A negative control sample includes a body fluid sample taken from a subject that is the same or homologous species as the subject to be assayed for POSTN fragments and is known to have normal biological state, e. g. without detectable POSTN fragments or a solution which does not contain POSTN fragments that are immunoreactive with at least one antibody according to the invention. A negative control sample includes a sample taken from a control subject. A positive control sample includes a body fluid sample taken from a subject that is the same or homologous species as the subject to be assayed for POSTN fragments and is known to have detectable POSTN fragments according to the invention or a solution which does contain POSTN fragments that are immunoreactive with at least one antibody according to the invention.

The term "antibody" as referred to herein designates a polypeptide that binds to an antigen. This includes whole antibodies and any antigen binding fragments. The term "antibody" is used in its broadest sense and includes monoclonal antibodies, polyclonal antibodies, human antibodies, humanized antibodies, chimeric antibodies, and further engineered antibodies as long as the characteristic properties of the invention are retained, in particular the ability of binding to the target antigen, more specifically to the epitope of POSTN fragment as the one recognized by the antibodies of the invention. Examples of antibodies and fragments thereof include a variable domain fragment ("Fv", consisting of the VH and VL domains of a single arm of an antibody), Fab fragment (monovalent fragment consisting of the VH, VL, CH1 and CL domains), Fab$_2$ fragment (bivalent), Fab$_3$ fragment (trivalent), Fab' fragment (Fab with hinge region), F(ab')$_2$ fragment (bivalent fragment including two Fab fragments linked by a disulfide bridge at the hinge region), Fd fragment (consisting of the VH and CH1 domains), rIgG (reduced IgG or half-IgG), diabodies, triabodies, tetrabodies, minibodies, monovalent antibodies, divalent or multivalent antibodies comprising a fragment of more than one antibody, single chain variable fragment (ScFv), bis-scFv (bispecific), and derivatives of antibodies such as disulfide stabilized Fv fragments, CDR-comprising peptides, as well as epitope-binding fragments of any of the above (Holliger and Hudson, 2005, *Nature Biotechnology,* 23(9): 1126-1136). An antibody refers to a glycoprotein comprising at least two heavy (H) chains and two light (L) chains inter-connected by disulfide bonds, or an antigen-binding fragment thereof. Each heavy chain comprises a heavy chain variable region (VH) and a heavy chain constant region (CH). Each light chain comprises a light chain variable region (VL) and a light chain constant region (CL). In mammalians, the heavy chain can either be alpha (α), delta (δ), epsilon (ε), gamma (γ) or mu (μ), which defines the class of antibody IgA, IgD, IgE, IgG and IgM, respectively. In mammalians, the light chain can either be lambda (λ) or kappa (κ). In mammalians, depending on the class of antibody, the heavy chain constant region comprises three immunoglobulin domains, CH1, CH2, and CH3 (for IgA, IgD, IgG) or four immunoglobulin domains, CH1, CH2, CH3, and CH4 (for IgE and IgM). The light chain constant region comprises one immunoglobulin domain, CL. An antibody can have the structure of an IgA, IgG, IgE, IgD and IgM as well as any subtype thereof. Antibodies may be from any source including in particular primate (human and non-human primate) and primatized sources. In particular, source may include non-primate animals, in particular s rabbits, mice, rats, wherein antibodies may be obtained by phage display technology.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "chimeric antibody" generally refers to an antibody comprising a variable region from one source or species and at least a portion of a constant region derived from a different source or species, usually prepared by recombinant DNA techniques. A typical example of chimeric antibodies includes those comprising a murine variable region and a human constant region.

The term "humanized antibody" designates antibodies from a non-human species having one or more complementarity determining regions (CDRs) from said non-human species and a framework region from a human immunoglobulin molecule. Humanized antibodies may optionally further comprise one or more framework residues derived from the non-human species from which the CDRs were derived.

The term "human antibody" or "fully human antibody" refers to antibodies in which the variable regions and the constant regions of both the heavy and the light chains are all of human origin, or substantially identical to sequences of human origin, but not necessarily from the same antibody.

The term "isolated antibody" refers to an antibody that has been separated from a component of its natural environment. For instance, an isolated antibody has been purified to greater than 95% or 99% purity as determined by methods in the art (see e.g. Flatman et al, 2007, *J Chromatogr B Analyt Technol Biomed Life Sci*, 848: 79-87) including electrophoretic (e.g. SDS-PAGE, isoelectric focusing, capillary electrophoresis) or chromatographic (e.g. ion exchange or reverse phase HPLC (high performance liquid chromatography) methods.

The terms "polynucleotide" or "nucleic acid molecule" refers to a polymer comprising nucleotides. Examples of nucleic acid molecules include DNA, RNA, locked nucleic acid (LNA), complementary DNA (cDNA).

The term "epitope" includes any antigenic determinant capable of specific binding to an antibody or antigen binding fragment thereof. An epitope is a region of an antigen that is bound by an antibody. Some epitopes comprise discontinuous sections of the antigen's amino acid sequence, where non-contiguous amino acids are positioned close to each other's by the spatial configuration of the antigen ("conformational epitopes") or comprise a section of contiguous amino acids on the antigen's amino acid sequence ("linear epitopes").

As used herewith the term "bind" or "binding" of an antibody to a target antigen means an at least temporary interaction or association of said antibody with, or to, said target antigen (such as POSTN fragments) or with, or to, fragments of said target antigen comprising an epitope recognized by said antibody.

The terms "selectively binds", "specifically binds", "specific for", when applied to an antibody, indicate that the antibody preferentially recognizes and/or binds the target polypeptide or epitope, i.e. with a higher affinity than to any other antigen or epitope, i.e. the binding to the target polypeptide can be discriminated from non-specific binding to other antigens. The binding affinity of an antibody can be readily determined by one of ordinary skill in the art, for example, by Scatchard analysis (Scatchard et al., 1949, *Ann. N.Y. Acad.* 1949. 51, 660-672).

As used herein, "binding affinity" generally refers to the apparent association constant or "Ka". The Ka is the reciprocal of the dissociation constant "Kd". Binding affinity may be determined by a variety of methods including equilibrium dialysis, equilibrium binding, gel filtration, ELISA, surface plasmon resonance or spectroscopy (e.g. using a fluorescence assay). Exemplary conditions for evaluating binding affinity are in TRIS-buffer (50 mM Tris-HCl, 150 mM NaCl, 5 mM CaCl2 at pH 7.5). These techniques can be used to measure the concentrations of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation: [Bound]=N×([Free])/((1/Ka)+[Free]). Comparison of affinity between two antibodies can be established without actually determining the Ka value for each antibody, but based on a quantitative measurement of affinity (e.g. by ELISA or FACS analysis) that is proportional to Ka or a qualitative measurement of affinity or an inference of affinity (e.g. in functional assay or in vitro or in vivo assay).

The term "solid matrix" includes any solid phase support suitable for carrying out an immunoassay or a method according to the invention. It includes beads, microparticles, nanoparticles, tubes, fabrics or plates, films, slides, wells, formed from or coated with glass, polystyrene, polypropylene, nitrocellulose, quartz, ceramic, dextran or other materials. For example, the solid matrix is in a form of microtiter wells, such as a 96-well microtiter plate or 386 wells plate. Solid matrix can be coated with coupling agent such as avidine and steptavidin.

The expression "kit" comprises at least one antibody according to the invention or a variant thereof or a combination thereof as described herein to be coupled or already coupled to a solid matrix and optionally instructional material.

As used herein a "metabolic bone disease or disorder" refers to any disease or disorder caused by abnormalities of minerals such as calcium, phosphorus, magnesium, vitamin D, parathyroid hormone (PTH) function or rare genetic mutations. Examples of metabolic bone disease or disorder include, but not limited to osteoporosis, osteomalacia (adults), rickets (children), osteitis fibrosa cystica, Paget's disease of bone, osteoclastogenesis dysfunction, osteopetrosis and sclerosing bone dysplasias, renal osteodystrophy, fibrous dysplasia, cancer induced bone diseases, primary hyperparathyroidism diseases, juvenile idiopathic osteoporosis and van Buchem disease.

As used herein "osteoporosis" refers to a disease where decreased bone strength increases the risk of a broken bone. It occurs due to the imbalance between bone resorption and formation. It is further characterised in a loss of bone mineral density and alterations in bone quality (microstructure and material properties) leading to fragility fractures.

The term "osteoclastogenesis dysfunction" as used herein refers to any condition related to increased bone turnover or bone resorption of secondary cause such a Paget's, bone loss resulting from immobilization, osteolytic bone metastasis, bone tumours, glucocorticoid-induced bone loss, hyperparathyroidism, hyperthyroidism and diabetes.

The term "subject" as used herein refers to mammals. For example, mammals contemplated by the present invention include human, primates, domesticated animals such as dogs, cats, cattle, sheep, pigs, horses, laboratory rodents and the like.

The term "patient" refers to a subject with a metabolic bone disease or disorder, such as osteoporosis.

The term "patient/subject at risk of osteoporosis" refers to a subject at risk of developing osteoporosis as confirmed e.g. by chemical biomarkers or by measuring the bone mineral density.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a metabolic bone disease or disorder in a mammal, particularly a human, and includes any use of any drug that targets osteoclasts or osteoblasts functions, including drugs targeting CatK metabolic pathway, e.g. CatK inhibitors, or drugs targeting sclerostin. In particular treatment of a metabolic bone disease or disorder in a mammal, particularly a human, may include administration of POSTN peptidic fragments.

The term "efficacy" of a treatment or method according to the invention can be measured based on changes in the course of disease or condition in response to a use or a method according to the invention. For example, the efficacy of a treatment or method according to the invention can be measured by its impact on signs or symptoms of illness. A response is achieved when the patient experiences partial or total alleviation, or reduction of unwanted symptoms of illness.

The term "effective amount" as used herein refers to an amount of at least one POSTN peptidic fragment, or a pharmaceutical formulation thereof, that elicits a detectable reduction of the symptoms of the disease in a subject that is being administered said POSTN peptidic fragment, these symptoms can include, for instance increase in bone density.

POSTN Fragments

According to one aspect of the invention are provided POSTN peptidic fragments obtainable after CatK-dependent degradation of POSTN.

In another aspect of the invention are provided POSTN peptidic fragments obtainable after CatK-dependent degradation of human POSTN, in particular human recombinant POSTN.

According to one aspect of the invention are provided POSTN fragments obtained by an in vitro method of CatK-dependent degradation.

In a particular embodiment, is provided an isolated peptide comprising or consisting of an amino acids sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

In a particular embodiment, is provided an isolated peptide consisting of 6 to 20 amino acid, comprising or consisting of an amino acids sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

In a particular embodiment, is provided an isolated peptide with a molecular weight ranging from about 600 to about 2400 Da, comprising or consisting of an amino acids sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

In a particular embodiment, is provided an isolated peptide consisting of 6 to 20 amino acid with a molecular weight ranging from about 600 to about 2400 Da, comprising or consisting of an amino acids sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

In a further embodiment, is provided an isolated peptide comprising or consisting of an amino acids sequence selected from the group consisting of: SEQ ID NO: 2, SEQ ID NO: 3, SEQ ID NO: 4 and SEQ ID NO: 5, or variants thereof.

In a further embodiment, is provided an isolated peptide comprising an amino-acid sequence of SEQ ID NO: 2.

In a further embodiment, is provided an isolated peptide consisting of an amino-acid sequence selected from the group consisting of: SEQ ID NO: 2, SEQ ID NO: 3, SEQ ID NO: 4 and SEQ ID NO: 5.

In a further embodiment, is provided an isolated peptide having at least 80%, at least 85%, at least 90%, at least 95%, at least 96%, at least 97%, at least 98% or at least 99% identity or homology with a sequence of amino acids selected from the group consisting of: SEQ ID NO: 2, SEQ ID NO: 3, SEQ ID NO: 4 and SEQ ID NO: 5. According to one aspect of the invention, is provided an isolated peptide having at least 80% identity or homology with a sequence of amino acids selected from the group consisting of: SEQ ID NO: 2, SEQ ID NO: 3, SEQ ID NO: 4 and SEQ ID NO: 5.

In another further embodiment, is provided an isolated peptide according to the invention having an amino acid sequence consisting of SEQ ID NO: 2, or variant thereof.

In another further embodiment, is provided an isolated peptide according to the invention having an amino acid sequence, wherein at least one amino acid is added or deleted at the C-terminal end.

In another further embodiment, is provided an isolated peptide according to the invention having an amino acid sequence, wherein at least two amino acids are added or deleted at the C-terminal end.

Methods of Producing POSTN Fragments

Synthetic chemistry methods, such as solid-phase peptide synthesis, can be used to synthesize the polypeptides according to the invention. Purification of those peptides may be carried out by means of any technique known in the art of protein/peptide purification. Exemplary techniques include ion-exchange chromatography, hydrophobic interaction chromatography, and immunoaffinity methods.

According to an embodiment, the invention provides a process of producing POSTN fragments or variants thereof according to invention comprising incubating POSTN of with CatK, in particular human CatK, such as human recombinant CatK.

According to an embodiment, the invention provides a process of producing POSTN fragments or variants thereof according to invention comprising incubating POSTN of with CatK, wherein POSTN and CatK are present at a ratio ranging from about 100:1 to about 22:1, wherein incubation process is performed at a temperature from about 19° to about 38°, wherein time of a reaction is from about 1 minute to about 24 h, and wherein said reaction is performed at pH from about 4 to about 6.

It is understood that both POSTN and CatK can be synthetic or derived from any species, in a preferred embodiment POSTN and CatK are human POSTN and CatK.

According to an embodiment, the invention provides a process of producing POSTN fragments or variants thereof according to invention comprising incubating human recombinant POSTN with CatK of SEQ ID NO: 19.

According to another embodiment, the process of producing POSTN fragments or variants thereof according to the invention comprising incubating human recombinant POSTN with CatK at a ratio ranging from about 100:1 to about 22:1.

The process of producing POSTN fragments or variants thereof according to the invention comprising incubating human recombinant POSTN with CatK at a ratio of 50:1.

The process of producing POSTN fragments or variants thereof according to the invention comprising incubating human recombinant POSTN with CatK at temperature from about 19 to about 38° C.

The process of producing POSTN fragments or variants thereof according to the invention comprising incubating human recombinant POSTN with CatK at temperature from about 35 to about 38° C.

The process of producing POSTN fragments or variants thereof according to the invention comprising incubating human recombinant POSTN with CatK at a temperature of about 37° C.

According to further embodiment, the process of producing POSTN fragments or variants thereof according to the invention comprising incubating human recombinant POSTN with CatK from about 1 minute to about 24 h.

According to further embodiment, the process of producing POSTN fragments or variants thereof according to the invention comprising incubating human recombinant POSTN with CatK from about 1 minute to about 5 h.

According to further embodiment, the process of producing POSTN fragments or variants thereof according to the invention comprising incubating human recombinant POSTN with CatK from about 10 minutes to about 60 minutes.

According to further embodiment, the process of producing POSTN fragments or variants thereof according to the invention comprising incubating human recombinant POSTN with CatK from about 10 minutes to about 30 minutes.

According to further embodiment, the process of producing POSTN fragments or variants thereof according to the invention comprising incubating human recombinant POSTN with CatK at pH from about 4 to about 6.

According to further embodiment, the process of producing POSTN fragments or variants thereof according to the invention comprising incubating human recombinant POSTN with CatK at pH of about 5.5.

POSTN Fragments Binding Antibodies

In one embodiment of the invention are provided isolated antibodies or antigen-binding fragments thereof specific for POSTN fragments according to the invention.

In one embodiment of the invention are provided isolated antibodies specific for POSTN fragments of the invention.

In an alternative embodiment of the invention are provided isolated antibodies or antigen-binding fragments thereof, specific for POSTN fragments of the invention, in particular human POSTN fragments as described herewith.

In an alternative embodiment of the invention are provided isolated antibodies or antigen-binding fragments thereof, specific for POSTN fragments, in particular human POSTN fragments, further characterized by their binding to an epitope on POSTN fragments, as described herewith.

The protein to which the antibodies according to the invention or fragments thereof, bind to POSTN fragments of the invention of any species.

The antibodies according to the present invention generally exhibit a high specificity for human POSTN fragments of the invention.

In a further embodiment, are provided isolated antibodies specific for a peptide of 6 to 20 amino acids comprising or consisting in an amino-acid sequence of SEQ ID NO: 2.

In a particular embodiment, the antibodies according to the invention, or fragments thereof, bind preferentially to POSTN fragments of the invention and exhibit a weak, or virtually no (i.e. negligible or not detectable), binding to full POSTN.

It is understood that any variant of an antibody according to the invention, or fragment thereof, that is described herewith is able to bind POSTN fragments of the invention. In a particular embodiment, such variant can show the same or even higher binding affinity for POSTN fragments of the invention, in comparison to the parental antibody or fragment from which said variant derives.

The antibodies according to the invention can be monoclonal antibodies, polyclonal antibodies, human antibodies, humanized antibodies, chimeric antibodies, and further engineered antibodies as long as the characteristic properties of the invention are retained, in particular the ability of binding to the target antigen, more specifically to the POSTN fragments of the invention.

In a particular embodiment of the invention, the antibodies specific for POSTN fragments according to the invention, or fragments thereof which specifically bind to POSTN fragments, are monoclonal antibodies.

In a particular embodiment of the invention, the antibodies specific for POSTN fragments according to the invention, or fragments thereof specifically bind to a POSTN fragment comprising or consisting of an amino acid sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

In a particular embodiment of the invention, the antibodies specific for POSTN fragments according to the invention, or fragments thereof specifically bind to a POSTN fragment consisting of 6 to 20 amino acid, comprising or consisting of an amino acid sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

In a particular embodiment of the invention, the antibodies specific for POSTN fragments according to the invention, or fragments thereof specifically bind to a POSTN fragment with a molecular weight ranging, from about 600 to about 2400 Da comprising or consisting of an amino acid sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

In a particular embodiment of the invention, the antibodies specific for POSTN fragments according to the invention, or fragments thereof specifically bind to a POSTN fragment consisting of 6 to 20 amino acid with a molecular weight ranging from about 600 to about 2400 Da comprising or consisting of an amino acid sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

In a preferred embodiment of the invention, the antibodies specific for POSTN fragments according to the invention, or fragments thereof specifically bind to peptide consisting or comprising an amino acid sequence selected from the group consisting of: SEQ ID NO: 2, SEQ ID NO: 3, SEQ ID NO: 4 and SEQ ID NO: 5.

In a more preferred embodiment of the invention, the antibodies specific for POSTN fragment according to the invention, or fragments thereof specifically bind to a peptide of an amino acid sequence consisting in SEQ ID NO: 2.

Antibodies can be produced by standard techniques in the field including the recovery of polyclonal antibodies from the serum of laboratory or farm animals, or eggs from chicken which have been injected with the antigen of interest, the recovery of monoclonal antibodies produced by fusing antibody-secreting spleen cells from immunized mice, or rats, or rabbits with immortal myeloma cell to create monoclonal hybridoma cell lines that express the specific antibody in cell culture supernatant. Alternatively, recombinant antibodies can be produced in various host cells including mammalian cells, plant cells, bacteria, yeasts, which have been engineered to express said antibodies.

In a particular embodiment of the invention, the antibodies specific for POSTN fragments according to the invention, or fragments thereof are produced by injecting synthetic POSTN fragment to rabbits and collecting serum thereof at defined intervals.

In a particular embodiment of the invention, the antibodies specific for POSTN fragments according to the invention, or fragments thereof are produced by phase-display technology after immunization of camelides.

In another aspect of the invention the POSTN fragments or variants thereof can be used as an immunogen for generating antibodies according to the invention.

The immunogens for generating antibodies according to the invention comprise a peptide comprising an amino acids sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

The immunogens for generating antibodies according to the invention comprise a peptide consisting of 6 to 20 amino acid, comprising an amino acids sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

The immunogens for generating antibodies according to the invention comprise a peptide with a molecular weight ranging from about 600 to about 2400 Da, comprising an amino acids sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

The immunogens for generating antibodies according to the invention comprise a peptide consisting of 6 to 20 amino acid with a molecular weight ranging from about 600 to about 2400 Da, comprising an amino acids sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18, or variants thereof.

According to a particular aspect, an immunogen for generating antibodies according to the invention is a peptide of 6 to 20 amino acids or consisting in an amino acid sequence of SEQ ID NO: 2.

Preferably, the immunogen for generating antibodies according to the invention is a peptide of an amino acid sequence selected from the group consisting of: SEQ ID NO: 2, SEQ ID NO: 3, SEQ ID NO: 4 and SEQ ID NO: 5, or variants thereof.

In another aspect of the invention, the isolated antibodies or fragment thereof according to the invention are optionally conjugated to an accessory molecule, and are then also referred to herein as "conjugated antibodies or "conjugated antibody fragments".

The accessory molecule may be conjugated to the antibody or antibody fragment directly or via a spacer of suitable length for instance as described in Kellogg et al., 2011, *Bioconjug Chem,* 22: 717-27).

In one embodiment, particularly adapted for diagnostic purposes, the accessory molecule can be, for example, a coupling agent such as biotin, a labeling group including radioisotopes (e.g. 3H, 14C, 32P, 35S, 125I), chromogenic labels, e.g. enzymes which can be used to convert a substrate to a detectable colored (e.g. horseradish peroxidase, alkaline phosphatase, β-galactosidase) or fluorescent compound (e.g. Green Fluorescent Protein, Red Fluorescent Protein), spectroscopic labels (e.g. fluorescent labels such as fluorescein and its derivatives like FITC, Texas red, cyanine dyes, photocyan, rhodamine, or labels presenting a visible color), luminescent labels including luciferins, affinity labels which may be developed by a further compound specific for the label and allowing easy detection and quantification, or any other label used in standard ELISA.

According to another embodiment, is provided a use of the antibodies according to the invention for the coating of a solid matrix for performing an immunoassay.

Nucleic Acids Encoding the Polypeptides of the Invention

According to one embodiment, is provided an isolated nucleic acid molecule encoding a peptide or variants thereof according to the invention.

According to one embodiment, is provided an isolated nucleic acid molecule encoding a POSTN fragments or variants thereof according to the invention.

The isolated nucleic acid according to the invention may be, for instance, natural DNA or RNA or a recombinant or synthetic DNA, RNA or LNA or a recombinant nucleic acid molecule comprising any of the nucleic acid molecules according to the invention either alone or in combination.

Nucleic Acids Encoding the Antibodies of the Invention

According to another embodiment, is provided an isolated nucleic acid molecule encoding an antibody or antigen-binding fragment thereof according to the invention.

In a particular embodiment, it is provided an isolated nucleic acid comprising a nucleic acid sequence encoding an antibody or antigen-binding fragment thereof according to the invention.

Vectors and Host Cells for Production and Purification of the Polypeptides of the Invention In one embodiment, the invention provides a recombinant expression vector comprising a nucleic acid molecule according to the invention, wherein the vector optionally comprises an expression control sequence, allowing expression in prokaryotic or eukaryotic host cells of the encoded polypeptide, operably linked to said nucleic acid molecule.

Numerous expression systems can be used, including without limitation chromosomes, episomes, and derived viruses. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses. These recombinant vectors can equally be cosmid or phagemid derivatives.

The nucleic acid sequence can be inserted in the recombinant expression vector by methods well known to a person skilled in the art such as, for example, those that are described in *MOLECULAR CLONING: A LABORATORY MANUAL*, Sambrook et al., 4th Ed., Cold Spring Harbor Laboratory Press, Cold Spring Harbor, N.Y., 2001.

The recombinant vector can include nucleotide sequences that allow, control or regulate the expression and the transcription of a polynucleotide of the invention as well as the translation of a polypeptide of the invention, these sequences being selected according to the host cells that are used.

Thus, for example, an appropriate secretion signal can be integrated in the recombinant vector so that the polypeptide, encoded by the nucleic acid molecule of the invention, will be directed towards the lumen of the endoplasmic reticulum, towards the periplasmic space, on the membrane or towards the extracellular environment. The choice of an appropriate secretion signal may facilitate subsequent protein purification.

In a further embodiment, it is provided a host cell comprising a recombinant vector according to the invention.

The introduction of the recombinant vector in a host cell can be carried out according to methods that are well known to a person skilled in the art, such as those described in *BASIC METHODS IN MOLECULAR BIOLOGY*, Davis et al., 2nd ed., McGraw-Hill Professional Publishing, 1995, and *MOLECULAR CLONING: A LABORATORY MANUAL*, supra, such as transfection by calcium phosphate, transfection by DEAE dextran, transfection, microinjection, transfection by cationic lipids, electroporation, transduction or infection.

The host cell can be, for example, bacterial cells such as *E. coli* or *Streptomyces*, cells of fungi such as *Aspergillus* and yeasts such as *Saccharomyces*, insect cells, Chinese Hamster Ovary cells (CHO), C127 mouse cell line, BHK cell line of Syrian hamster cells, Human Embryonic Kidney 293 (HEK 293) cells. In a particular embodiment, the host cell is a CHO cell or a HEK 293 cell.

The host cells can be used, for example, to express a polypeptide of the invention. After purification by standard methods, the polypeptide of the invention can be used in a method described hereinafter.

For instance, when expression systems that secrete the recombinant protein are employed, the culture medium may first be concentrated using a commercially available protein concentration filter, for example, an Amicon or Millipore Pellicon ultrafiltration unit. Following the concentration step, the concentrate can be applied to a purification matrix such as a gel filtration matrix. Alternatively, an anion exchange and/or an affinity resin can be employed. The matrices can be acrylamide, agarose, dextran, cellulose or other types commonly employed in protein purification. Alternatively, a cation exchange step can be employed. Finally, one or more reversed-phase high performance liquid chromatography (RP-HPLC) steps employing hydrophobic RP-HPLC media can be employed to further purify the antibodies or fragments thereof. Some or all of the foregoing purification steps, in various combinations, are well known and can be employed to provide a substantially homogeneous recombinant protein.

Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Microbial cells can be disrupted by any convenient method, including freeze-thaw cycling, sonication, mechanical disruption, or use of cell lysing agents.

In another embodiment, the invention provides a process for producing cells capable of expressing a polypeptide according to the invention, comprising genetically engineering cells with a vector or a nucleic acid according to the invention.

In another embodiment, the invention provides a process for producing peptides according to the invention comprises culturing a host cell transformed with an expression vector comprising a nucleic sequence that encodes said antibodies or fragments thereof under conditions sufficient to promote expression of said polypeptides. The peptides according to the invention are then recovered from culture medium or cell extracts, depending upon the expression system employed.

In another embodiment, the invention provides a process for producing antibodies or fragments thereof according to the invention comprises culturing a host cell transformed with an expression vector comprising a nucleic sequence that encodes said antibodies or fragments thereof under conditions sufficient to promote expression of said polypeptides. The antibody or fragment thereof according to the invention is then recovered from culture medium or cell extracts, depending upon the expression system employed. As known to the skilled artisan, procedures for purifying a recombinant protein will vary according to such factors as the type of host cells employed and whether or not the recombinant protein is secreted into the culture medium as described above.

Compositions

The invention provides pharmaceutical or therapeutic agents as compositions and methods for treating a patient, preferably a mammalian patient, and most preferably a human patient who is suffering from a medical disorder, and in particular a metabolic bone disorder. Alternatively, the invention provides methods for preventing a medical disorder, and in particular a metabolic bone disorder.

In one embodiment, is provided a pharmaceutical composition comprising one or more of (i) peptide according to the invention or fragment thereof, (ii) a nucleic acid according to the invention, (iii) a vector according to the invention, and/or (iv) a host cell according to the invention, and at least one pharmaceutically acceptable carrier. Pharmaceutical compositions of the invention can contain one or more peptide of the invention or fragment thereof in any form described herein.

Compositions of this invention may further comprise one or more pharmaceutically acceptable additional ingredient(s) such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, freeze-dried forms, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Compositions of this invention may be liquid formulations including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agent include, but are not limited to, sorbitol syrup, methylcellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's The Science and Practice of Pharmacy*, 22$^{nd}$ Edition, 2012, Pharmaceutical Press and the University of the Sciences, Philadelphia College of Pharmacy, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as transdermal formulations comprising aqueous or non-aqueous vehicles including, but not limited to, creams, ointments, lotions, pastes, medicated plaster, patch, or membrane.

Compositions of this invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

The compounds of this invention can also be administered in sustained release forms or from sustained release drug delivery systems. A description of representative sustained release materials can also be found in the incorporated materials in *Remington's Pharmaceutical Sciences*.

Injectable formulations are particularly appropriate for administering the compositions according to the invention.

In another embodiment, the invention provides an imaging composition or diagnostic composition comprising an antibody or an antigen-binding fragment thereof specific for at least one peptide of the invention or variant thereof as described herewith.

In another embodiment, the invention provides a diagnostic composition comprising an antibody or antigen-binding fragment thereof specific for a peptide of the invention or variant thereof as described herewith for detection of a peptide of the invention or variants thereof.

In one embodiment, diagnostic composition according to the invention comprise an antibody or antigen-binding fragment thereof specific for a peptide of the invention or variant thereof as described herewith conjugated to a moiety selected from the group consisting of a radioisotope, a biotin, an avidin, a strepavidin, a chromophore, a fluorophore, a chemiluminescent moiety, a hapten and an enzyme.

The imaging composition or diagnostic composition according to the invention is useful for detecting elevated levels of a peptide of the invention or variant thereof associated with metabolic bone diseases.

Combination

According to the invention, peptides or variant thereof according to the invention can be administered alone or in combination with a co-agent useful in the prevention and/or treatment of an metabolic bone disorder, for example immune modulatory drugs including biologics, small molecules, and vaccines.

Peptides of the invention or variant thereof can be administered to an individual prior to, simultaneously or sequentially with other therapeutic regimens or co-agents useful in the prevention and/or treatment of a metabolic bone disease. The peptides of the invention or variant thereof according to the invention that are administered simultaneously with said co-agents can be administered in the same or different compositions and in the same or different routes of administration.

Mode of Administration

Compositions of this invention may be administered in any manner including, but not limited to, orally, parenterally, sublingually, transdermally, rectally, transmucosally, topically, via inhalation, via buccal or intranasal administration or intra bladder, or combinations thereof.

Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion.

In a particular embodiment, peptides of the invention or variant thereof according to the invention are administered systemically or locally.

In a particular embodiment, a peptide of the invention or variant thereof according to the invention is administered by subcutaneous or intravenous route.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Methods According to the Invention

In another aspect, the invention provides an immunoassay preparation comprising at least one antibody according to the invention.

According to a particular aspect, an immunoassay preparation according to the invention can be used in a method for the detection of POSTN fragments, such as a method of measuring detection of POSTN fragments contained in a sample.

Examples of a method utilizing an antigen-antibody reaction in detection of POSTN fragments contained in a sample include enzyme immunoassays (ELISA and EIA), fluoroimmunoassays (FIAs), radioimmunoassays (RIAs), luminescence immunoassays (LIAs), enzyme antibody techniques, fluorescence antibody techniques, immunochromatographies, immunonephelometries, latex nephelometries, latex agglutination assays, erythrocyte agglutination assays, particle agglutination assays, the method described in, for example, Japanese Patent Laid-Open No. H09-229936 or Japanese Patent Laid-Open No. H10-132819 using a carrier having a surface onto which a substance that specifically binds to a substance to be measured (analyte) is immobilized so as to cover the surface and using particles onto which a substance that specifically binds to the substance to be measured (analyte) is immobilized, and the enzyme-linked ligandsorbent assay (ELSA) described by Dahlbeack et al., 1998, *Thromb. Haemost.*, 79, 767-772; WO 98/23963).

According to an embodiment, the invention provides a method for detecting a POSTN fragment from a biological fluid sample of a mammalian subject comprising the steps of:
(a) providing a biological fluid sample obtained from a mammalian subject;
(b) bringing the said biological fluid sample into contact with a solid matrix where at least one antibody is bound to, wherein the contacting is under conditions sufficient for binding a POSTN fragment present in the said biological fluid sample to the said at least one antibody through antigen-antibody interactions and wherein the said at least one antibody is specific for POSTN fragment or any variant thereof;
(c) removing the biological fluid sample from the solid matrix for removing any unbound POSTN fragment from the surface of the said solid matrix;
(d) detecting the presence of an antigen-antibody complex bound to the said solid matrix, wherein the presence of the said complex is indicative that the biological fluid sample contains one or more POSTN fragments.

According to an embodiment, the invention provides a method for detecting a POSTN fragment from a biological fluid sample of a mammalian subject comprising the steps of:
(a) providing a biological fluid sample obtained from a mammalian subject;
(b) bringing said biological fluid sample into contact with at least one antibody, wherein the contacting is under conditions sufficient for binding a POSTN fragment of the invention present in said biological fluid sample to said at least one antibody through antigen-antibody interactions and wherein said at least one antibody is specific for POSTN fragment of the invention or any variant thereof;
(c) bringing sample obtained under step b) into contact with a solid matrix where at least one POSTN fragment of the invention is bound to, wherein the contacting is under conditions sufficient for binding an antibody specific for POSTN fragment of the invention present in said sample to said at least one POSTN fragment of the invention through antigen-antibody interactions;
(d) washing the solid matrix for removing any unbound antibody from the surface of the said solid matrix;
(e) detecting the presence of an antigen-antibody complex bound to the said solid matrix, wherein the presence of the said complex is indicative that the biological fluid sample contains one or more POSTN fragments of the invention.

In another aspect, the invention provides a method for detecting a POSTN fragment from a biological fluid sample of a mammalian subject comprising the steps of:
(a) providing a biological fluid sample obtained from a mammalian subject;

(b) providing a solid support having bound thereto at least one POSTN fragments of the invention;
(c) bringing said solid support into contact with said biological fluid sample;
(d) bringing said solid support into contact with at least one antibody specific for POSTN fragment of the invention or any variant thereof, wherein the contacting is under conditions sufficient for binding a POSTN fragment of the invention present in said biological fluid sample to said at least one antibody through antigen-antibody interactions;
(e) washing the solid matrix for removing any unbound antibody from the surface of the said solid matrix;
(f) detecting the presence of an antigen-antibody complex bound to the said solid matrix, wherein the presence of the said complex is indicative that the biological fluid sample contains one or more POSTN fragments of the invention.

According to an embodiment, a solid support having bound thereto at least one POSTN fragment of the invention can be obtained by coating a microtiter plate with at least one POSTN fragment of the invention or by modifying a surface of a microtiter plate to be covalently conjugated to at least one POSTN fragment of the invention. For example, biotinylated peptides of the invention can be incubated on streptavidin pre-coated microplates according to standard methods.

According to an embodiment, the detection of the presence of an antigen-antibody complex bound to the solid matrix can be achieved with a secondary antibody. According to an embodiment, a method for detecting a POSTN fragment according to the invention is indicative of a metabolic bone disorder in said subject.

According to an embodiment, a method for detecting a POSTN fragment according to the invention is indicative of the effect of treatment of a metabolic bone disorder in said subject.

According to a further embodiment, is provided a method according to the invention, wherein said at least one antibody is specific for a peptide comprising or consisting in sequence of amino acid selected from: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18.

According to a further embodiment, is provided a method according to the invention, wherein said at least one antibody is specific for a peptide consisting of 6 to 20 amino acid, comprising a or consisting in sequence of amino acid selected from: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18.

According to a further embodiment, is provided a method according to the invention, wherein said at least one antibody is specific for a peptide with a molecular weight ranging from about 600 to about 2400 Da, comprising a or consisting in sequence of amino acid selected from: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18.

According to a further embodiment, is provided a method according to the invention, wherein said at least one antibody is specific for a peptide consisting of 6 to 20 amino acid with a molecular weight ranging from about 600 to about 2400 Da, comprising a or consisting in sequence of amino acid selected from: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18.

According to a further embodiment, is provided a method according to the invention, wherein said at least one antibody is specific for a peptide comprising or consisting in a sequence of amino acids selected from: SEQ ID NO: 2, SEQ ID NO: 3, SEQ ID NO: 4 and SEQ ID NO: 5.

According to a further embodiment, is provided a method according to the invention, wherein said at least one antibody is specific for a peptide comprising or consisting in a sequence of amino acids of SEQ ID NO: 2.

According to another further embodiment, is provided a method according to the invention, wherein the said biological fluid sample is brought into contact with the said solid matrix under step b), where at least one antibody or variant thereof according to the invention is bound to said solid matrix.

According to another further embodiment, is provided a method according to the invention, wherein a known quantity of capture antibody is bound to said solid matrix under step b).

According to another further embodiment, is provided a method for detecting a POSTN fragments from a biological fluid sample of a mammalian subject wherein the said biological fluid sample is brought into contact with the said solid matrix under step b), where a combination of antibodies or of variants thereof is bound to the said solid matrix and where the combination comprises: a) one antibody specific for a peptide having a sequence of amino acids of SEQ ID NO: 2 or a variant thereof; and b) at least one antibody specific for a peptide having an amino acid sequence selected from: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18 or a variant thereof.

According to another further embodiment, is provided a method for detecting a POSTN fragments from a biological fluid sample of a mammalian subject wherein the said biological fluid sample is brought into contact with the said solid matrix under step b), where a combination of antibodies or of variants thereof is bound to the said solid matrix and where the combination comprises: a) one antibody specific for a peptide having a sequence of amino acids of SEQ ID NO: 2; and b) at least one antibody specific for a peptide having a sequence of amino acids selected from: SEQ ID NO: 3, SEQ ID NO: 4 and SEQ ID NO: 5.

According to another further embodiment, is provided a method according to the invention, wherein the method further comprises a step of comparing the signal obtained under the detection step d) with the same signal obtained for at least one control sample, wherein the signal obtained for the said at least one control sample is collected previously, simultaneously or posteriori to the detection step d) for the said biological fluid sample.

Detection of the captured/bound POSTN fragments under step d) by any suitable method known in the art for detecting captured antibodies or proteins on surfaces such as optical detection (e.g. ELISA), mass variation detection (e.g. surface Plasmon resonance, mass spectrometry), electrical detection (e.g. impedance spectroscopy, electrochemical) techniques. Results of the assay may be qualitative or quantitative. The amount of POSTN fragments associated with antibodies can be compared with positive and negative controls. The controls are typically run concomitantly with the sample to be tested. A positive control can be a serum or a solution containing a POSTN fragment that is immunoreactive with at least one antibody according to the invention. A negative control can be a serum or solution which does not contain a POSTN fragment that is immunoreactive with at least one antibody according to the invention. For quantization, a calibration curve using known quantities of POSTN fragments to at least one antibody according to the invention can be generated and/or used.

The comparison with normal healthy biological fluid samples may be achieved with different methods. According to one embodiment, it may be carried out by including a control reaction with a blood sample from healthy subject. According to another embodiment, it may be carried out by employing a value for the concentration of the endogenous POSTN fragments for a typical biological fluid sample from a healthy subject. Typically, the comparison of the level of endogenous POSTN fragments present in a sample under investigation may be performed with respect to a value determined in each single testing procedure or to a predetermined value. The predetermined value may be determined for the testing procedure in general, or alternatively, the value may be valid only for a certain batch of testing reagents. For example, the reference value may be valid for a defined calibration period only and may be redefined upon calibration of the testing process.

According to another further embodiment, is provided a method of monitoring the effects of a treatment of subjects with osteoporosis comprising detection of POSTN fragments.

According to another further embodiment, is provided a method of monitoring progression of treatment of patients with osteoporosis comprising detection of POSTN fragments.

According to another further embodiment, is provided a method of diagnosis of patients at risk of osteoporosis comprising detection of POSTN fragments.

According to another further embodiment, is provided a method of diagnosis of subjects with a metabolic bone disorder comprising detection of POSTN fragments.

According to another further embodiment, is provided a method of monitoring the effects of a treatment of subject with a metabolic bone disorder comprising detection of POSTN fragments.

According to a further embodiment, are provided methods according to the invention wherein a metabolic bone disorder is osteoporosis.

According to a further embodiment, is provided a method according to the invention, wherein said method is an ex vivo method.

According to another further embodiment, is provided a method for preventing and/or treating of subjects with a metabolic bone disorder comprising administering an isolated peptide POSTN fragment or variants thereof.

Kit and Method Using Thereof

According to one aspect, the invention relates to a kit for carrying out a method according to the invention.

According to one aspect, the invention provides a kit for detecting the formation of Cat K proteolytic fragments of POSTN in the bone cortical compartment.

According to a further aspect, the invention provides a kit comprising (1) a solid support having bound thereto at least one POSTN fragment of the invention; and optionally: (2) at least one antibody according to the invention specific for said at least one POSTN fragment; (3) at least one unbound POSTN fragment of the invention to serve as positive control; (4) at least one detection agent for detecting the complex that forms between said at least one POSTN fragment of the invention present in a biological sample and said at least one antibody according to the invention specific for said at least one POSTN fragment.

According to a particular aspect, the invention provides an ELISA kit, more particularly a competitive ELISA kit.

According to another aspect of the invention, is provided a kit comprising at least one antibody according to the invention or a variant thereof.

According to another aspect of the invention, is provided a kit for detecting a POSTN fragment of the invention in a biological fluid sample, the kit comprising at least one antibody according to the invention or a variant thereof.

The kit according to the invention comprises at least one antibody according to the invention, a variant thereof or a combination thereof for coupling, or already coupled to a solid matrix as solid phase support as referred herein. Various solid matrices can be used, including but not limited to glass, polystyrene, polypropylene, nitrocellulose, quartz, ceramic, dextran or other materials. Suitable forms of the solid matrix include beads, microparticles, nanoparticles, tubes, fabrics or plates, films, slides, wells, formed from or coated with these materials. Typically, the solid matrix comprises microtiter wells, such as a 96-well microtiter plate.

An antibody of the invention can be immobilized onto a solid-phase carrier by adsorption and/or binding through a known method such as physical adsorption, chemical binding, or the both.

According to another further embodiment, is provided a use of a kit of the invention for the detection of a metabolic bone disorder in a subject or for monitoring the course of a treatment of said disorder in a subject.

According to another further embodiment, is provided a use of a kit of the invention for detecting a POSTN fragment in a biological fluid sample.

The method, the kit and uses according to the invention may be suited for screening purposes as well as for diagnostic purposes and may be applied in primary diagnosis as well as in monitoring of disease course during or after treatment.

According to a particular aspect, the detection of a one or more POSTN fragment(s) according to the invention, in particular a fragment comprising or consisting in a sequence of a peptide according to SEQ ID NO: 2 is a biomarker of the bone quality and is indicative of a risk of fracture in a subject. The detection of such fragment(s) by antibodies specific for the fragment(s) is particularly useful in a method or a use according to the invention.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention. The examples illustrating the invention are not intended to limit the scope of the invention in any way.

EXAMPLES

Ahx (2-aminohexanoic acid), AUC (area under the curve), BSA (bovine serum albumin), BMD (Bone mineral density), BMI (body mass index), BV/TV (bone volume on total volume), CatK (Cathepsin K), CI (confidence interval), Ct. (cortical bone), Ct.Th (Ct thickness), CTX (cross-linked C-terminal telopeptide of type I collagen), CV (coefficient of variability), DXA (dual-energy x-ray absorptiometry), Ec (endocortical surface), FRAX (fracture risk assessment tool), HRP (horseradish peroxidase), KLH (keyhole limpet hemocyanin), LC-MS/MS (liquid chromatography-tandem mass spectrometry), MI (moment of inertia), MI (moment of inertia), MW (Molecular weight), OD (optical density), P1NP (procollagen type 1 N-terminal propeptide), POSTN (periostin), Ps (periosteum surface), ROC (Receiver Operating Characteristic curve), RT (room temperature), SD (standard deviation), SDS-PAGE (sodium dodecyl sulfate-polyacrylamide gel electrophoresis), sPOSTN (serum POSTN), STD (Standard), Tb. (trabecular bone), TRIS (Tris(hydroxymethyl) aminomethane), TBS (Tris-buffered saline), vBMD (volumetric bone mineral density).

Example 1

CatK Digestion of Human POSTN

To identify the human POSTN fragments resulting from CatK dependent digestion lasting 1 h, 2 h, 3 h or overnight, polyacrylamide gel electrophoresis was used on POSTN protein sample mixed with an anionic detergent (sodium dodecyl sulfate) (SDS-PAGE).

CatK digestion, targeted LC-MS/MS and silver stained SDS-PAGE. Human recombinant POSTN (1.1 µM) was incubated with human CatK of SEQ ID NO: 19 (2.24 µM) at 37° C. Times and POSTN/CatK ratios are indicated for each protocol below. The inhibitor E64 (250 µM) was added to stop the digestion at the end of incubation. Then, the digests were analyzed by SDS-Page electrophoresis. Various POSTN fragments bands were excised from the SDS-Page gel and digested with trypsin. Then, the tryptic peptides were concentrated and separated by reverse phase chromatography on a PepMap100, C18, 5 µm, 100 Å, 300 µm×25 mm column from Dionex (ThermoScientific) using a gradient of 5 to 40% acetonitrile, 0.1% formic acid in 60 min at 300 nL/min. Furthermore, to maximize the sequence coverage, the analysis was conducted on 2 mass spectrometers, LTQ Velos Mass Spectrometer (ThermoScientific) and Qstar XL Mass Spectrometer (Applied Biosystems).

About 105 of unique POSTN fragments were observed after CatK digestion of POSTN lasting 3 h. POSTN fragments observed after CatK digestion corresponded to 62% of POSTN sequence. Several POSTN fragments were characterised by overlapping sequences indicating a non-specific type of cleavage by enzyme CatK. Two protein bands of POSTN fragments were detected of about 35kDa and 7 kDa (FIG. 2A). The bands were not observed in negative control where no enzyme was added to POSTN (FIG. 2A). Digestion of constant amount of POSTN with increasing amount of CatK indicates that the abundance ratio of POSTN fragments increased with increasing amount of enzyme, saturating at a ratio lower than POSTN/CatK of 11:1 (FIG. 2B).

This data show that human POSTN is a substrate to CatK-dependent enzymatic digestion that is generating large amount of several peptides which may serve as markers of CatK activity in periosteum.

Example 2

Identification of POSTN Fragments

Several CatK-dependent POSTN fragments were separated and identified with the use of targeted liquid chromatography-tandem mass spectrometry (LC-MS/MS).

CatK digestion, targeted LC-MS/MS and silver stained SDS-PAGE as described in Example 1. Twenty-one different POSTN fragments were separated in a single LC-MS/MS analysis (FIG. 3A) which included peptides 1-17 which were further analysed below and peptide 18 (SEQ ID NO: 22), peptide 19 (SEQ ID NO: 23), peptide 20 (SEQ ID NO: 24) and peptide 21 (SEQ ID NO: 25). The most abundant CatK-digested POSTN fragments of SEQ ID NO: 2 and SEQ ID NO: 6 obtained at a ratio POSTN/CatK ranging from 250:1 to 5:1 were measured with LC-MS/MS. Absence of an incomplete digested POSTN fragment (ID SEQ NO.: 6) served as an indication of complete POSTN digestion at POSTN/CatK ratio of 5:1 (FIG. 3B).

This data show that the optimal in vitro digestion of human POSTN appears at POSTN/CatK ratio within a range of 100:1 to 22:1. The most abundant CatK-digested POSTN fragments are of SEQ ID NO: 2 and SEQ ID NO: 6.

Example 3

Time Course of CatK-Dependent POSTN Digestion

Time course of appearance of 17 CatK-dependent POSTN fragments obtained at POSTN/CatK ratio of 50:1, separated and identified with the use of LC-MS/MS, was evaluated.

Figure 4:
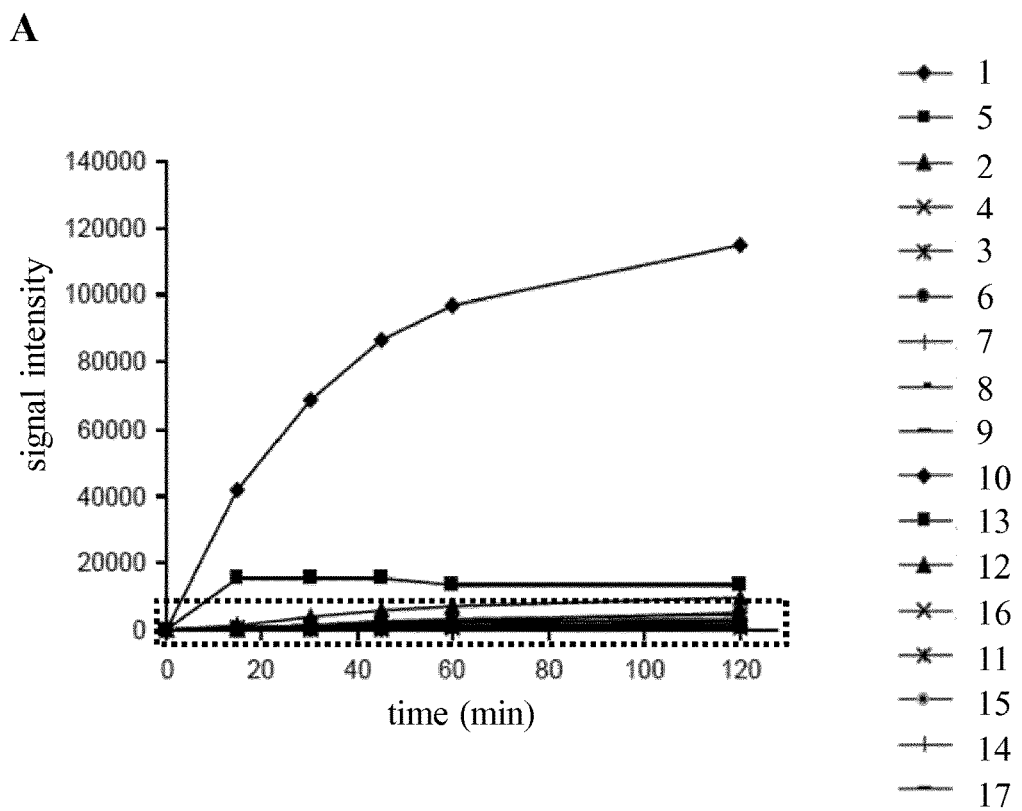
FIG. 4 shows the time course of POSTN fragments appearance between 15 min to 2 h during CatK-dependent POSTN digestion as described in Example 3, at POSTN/CatK ratio of 50:1. A: the dotted area is shown on panel B. POSTN fragments indicated as in FIG. 3.

CatK digestion, targeted LC-MS/MS and silver stained SDS-PAGE as described in Example 1. The appearance of 17 different POSTN fragments were monitored during CatK-dependent POSTN digestion between 15 min to 2 h, at POSTN/CatK ratio of 50:1 (FIG. 4). The earliest fragment is of SEQ ID NO: 2 appearing within 15 min from reaction start, followed by fragments of SEQ ID NO: 6, SEQ ID NO: 3, SEQ ID NO: 4, SEQ ID NO: 7 and SEQ ID NO: 5. Most of the POSTN digestion finishes within 60 min from the start of reaction.

Those 17 POSTN fragments were then ranked based on their abundance as measured in LC-MS/MS analysis, as well as speed of their generation (FIG. 5). Sequences of observed POSTN fragments suggest that amino acids K, T, E, R and L are preferred cleavage sites for CatK-digested of POSTN in order of preference as follows K>T>E>R>L.

The most abundant and fastest appearing CatK-digested POSTN fragments are of SEQ ID NO: 2, SEQ ID NO: 6, SEQ ID NO: 3, SEQ ID NO: 4, and SEQ ID NO: 5. Therefore, these are preferred POSTN fragments that could be useful to mark activity of CatK in bone.

Example 4

Production of Anti-POSTN Fragments Antibodies

Antibodies are generated by conventional immunization protocols. Specifically, peptides of the invention are coupled to a carrier molecule, including but not limited to, keyhole limpet hemocianin and bovine serum albumin (BSA). Peptide fragments, once coupled are then injected into rabbits for 55 days. The serum of the animals is collected and purified by immunoaffinity methods against the POSTN fragments.

Immunization. Two rabbits (H8308 and H8325) were immunized by injection of the synthetic peptide comprising amidated peptide of SEQ ID NO: 2, cysteine (C; to allow a conjugation at the N-terminal end) and 2-aminohexanoic acid (Ahx, hydrophobic spacer allowing better exposure of the specific sequence), and referred to as C-Ahx-GSLQ-PIIK-NH$_2$, which was further coupled with keyhole limpet hemocyanin (KLH).

Antibody purification and characterization. The antibodies were isolated from serum of the animals by immunoaffinity using a gel coupled with the sequence of peptide 1. Titer of immunopurified antiserum was evaluated by direct binding on peptide of SEQ ID NO: 2 coupled to bovine serum albumin (BSA), referred to as BSA-GSLQPIIK. The titer of obtained antiserum was evaluated to be at about $10^6$, supporting that a polyclonal antibody specific to CatK-digested POSTN fragment of SEQ ID NO: 2 was isolated. Due to the high sequence homology between human POSTN and POSTN of other species, those antibodies may react with mouse, rat, cynomolgous monkey, dog and cat POSTN fragments.

Example 5

CatK-Digested POSTN Fragment Presence in Cortical Mouse Bone

The presence of CatK-digested POSTN fragments of SEQ ID NO: 2 were assessed in mouse bone using the antibodies prepared according to Example 4.

Immunohistochemical analysis. The right and left tibiae were excised from mouse and subsequently fixed in 4% paraformaldehyde overnight at 4° C. They were then decalcified in 19% ethylenediaminetetraacetic acid (EDTA) and 4% phosphate-buffered formalin for 3 weeks. The tibiae were then dehydrated in an ascending series of ethanol, cleared in Propar (Anatech LTD, Battle Creek, Mich.), and embedded in paraffin blocks. 8 µm-thick sections were cut from the blocks at the tibia mid-shaft level using a RM2155 microtome (Leica, Germany) and mounted on Superfrost Plus slides (Fisher Scientific, Pittsburg, Pa.). Sections were air-dried overnight at room temperature. Prior to staining, sections were incubated in an oven (Hybaib, MGW Biotech) at 60° C. for 1 h, deparaffinized in xylene, and rehydrated in a descending series of ethanol. De-paraffinized slides were pre-treated in 3% hydrogen peroxide in methanol to quench endogenous peroxidase and rinsed in tap water followed by non-specific avidin/biotin blocking (Vector Laboratories, Burlingame, Calif.) according to the manufacturer's directions. All incubations took place in a humidified chamber. Additional protein blocking was accomplished with Protein Block-Serum Free (DAKO, Carpinteria, Calif.). Using the Vectastain Elite ABC (Rabbit IgG) Kit (Vector Laboratories, Burlingame, Calif.), the slides were incubated in 1.5% normal goat serum for 30 minutes at room temperature. The primary antibody (antibody to CatK-digested POSTN fragment of SEQ ID NO: 2 as obtained in Example 4 was diluted in Antibody Diluent (DAKO, Carpinteria, Calif.) to a final concentration of 1/200000 and 1/10000 and incubated at 4° C. overnight. The following day, slides were rinsed in Wash Buffer (DAKO, Carpinteria, Calif.) for 15 min on a rocker at room temperature and incubated in biotinylated goat anti-rabbit (Vectastain Kit) secondary antibody diluted 1:1000 for 30 min at room temperature, followed by another rinse in Wash Buffer for 15 min on a rocker at room temperature. The ABC reagent from the Vector Kit was prepared according to the manufacturer's directions at a dilution of 1:250 and the slides were incubated in it for 30 min at room temperature and rinsed, as above, in DAKO® Wash Buffer. All incubation steps were performed at room temperature and all rinse steps employed the DAKO® Wash Buffer at room temperature on a rocker. Next, slides were incubated in streptavidin- horseradish peroxidase (HRP) diluted at 1:100 for 30 min, and washed for 15 min. Slides were developed in a working solution of 3,3'-diaminobenzidine (DAB Substrate Kit for Peroxidase Kit, Vector Laboratories, Burlingame, Calif.) prepared according to manufacturer's directions for 10 min at room temperature. Following a final rinse in deionized water, the slides were mounted in Cytoseal 60 (Richard-Allan Scientific, Kalamazoo, Mich.). For the negative control, primary antibody incubation have been replace by TRIS 0.1M. Digital images were obtained using a microscope with a camera AxioCam MRc5 controlled by Axiovision AC software (Carl Zeiss MicroImaging GmbH, Germany).

Figure 6:
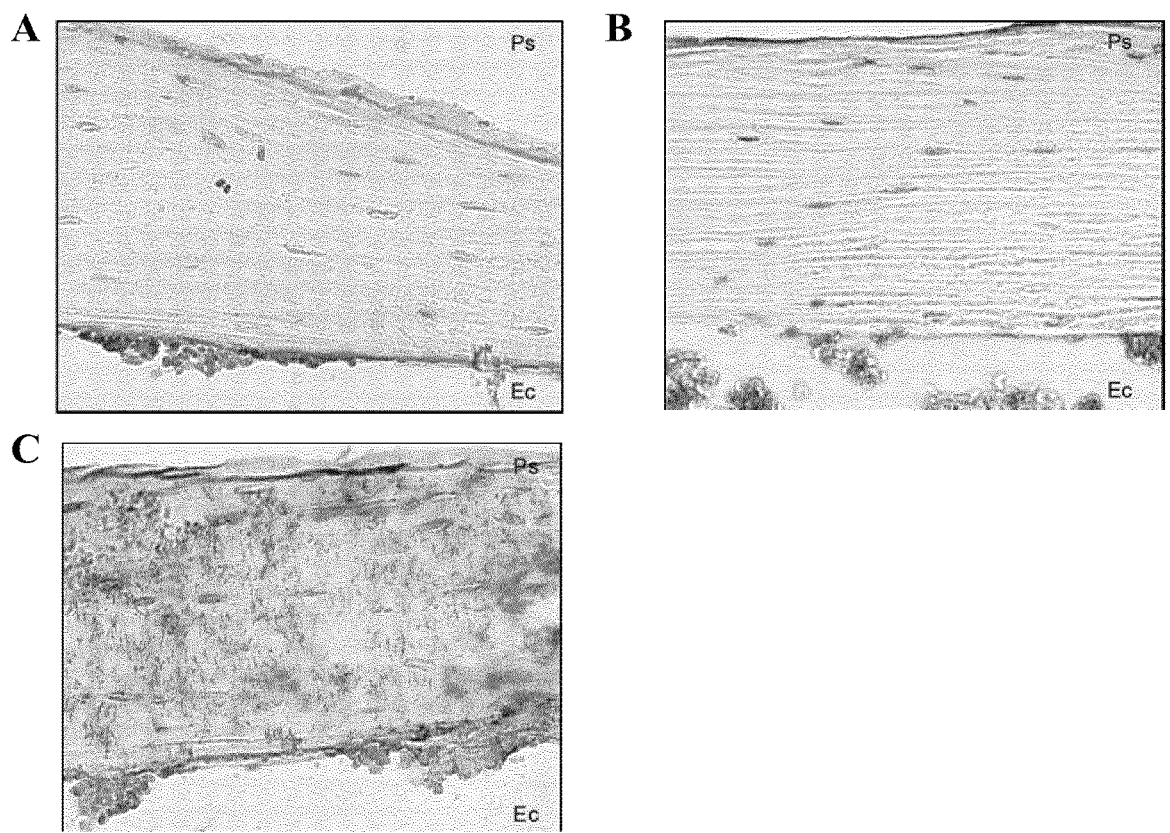
FIG. 6 shows immunostaining of osteocytes and lacuno canalicular system from mouse bone detected in presence of anti-SEQ ID NO: 2 as described in Example 6. A: control; B: in presence of anti-SEQ ID NO: 2 antibodies at 1/200000; C: in presence of anti-SEQ ID NO: 2 antibodies at 1/10000.

The presence of CatK-digested POSTN fragments of SEQ ID NO: 2 was detected at mouse periosteum surface (Ps) of cortical bone region, specifically in osteocytes and lacuno canalicular system as well as in the bone matrix with the use of anti-SEQ ID NO: 2 antibodies used at the concentration of 1/10000, but not at the concentration of 1/200000 (FIG. 6).

This analysis confirmed that the antibodies of the invention are able to detect the presence of CatK-digested POSTN fragments of SEQ ID NO: 2 in mouse osteocytes and lacuno canalicular system of cortical bone region and that these fragments are specific for this bone region.

Example 6

ELISA Assay for a CatK-Digested POSTN Fragment

An ELISA assay was developed for assaying CatK-digested POSTN peptidic fragments of the invention. First, biotinylated peptides are prepared by conjugating a peptide of the invention to be assayed with biotin. Those biotinylated POSTN peptides (e.g. 100 µl) are incubated on streptavidin coated microtiter plates (for 2 h, at room temperature, in coating buffer) to coat the plates with a peptide. After washing off the excess of POSTN peptide used as calibrator (3-5 times with BSA-Tween blocking solution in TBS buffer), the sample to be tested (standard solution of the unmodified POSTN peptide to be assayed, or a buffer sample used as control solution or a serum sample) is added to each well. Primary anti-POSTN peptide antibodies prepared as described in Example 4 and specific for the POSTN peptide fragment to be assayed are also added. For example, 50 µl of standard (synthetic POSTN peptide to be assayed) at different concentrations of 0, 1, 5, 10, 50, 100, 500, 1000 ng/ml or serum sample and 50 µl of primary H8308/H8325 antibody in assay buffer is added and incubated overnight at 4° C. After incubation, the plates are washed (e.g. 3-5 times with BSA-0.05% Tween blocking solution in TBS buffer) and a solution of peroxidase-conjugated goat anti-rabbit antibody (secondary antibody) is pipetted into each well (e.g. 100 µl of horseradish peroxidase-conjugated goat anti-rabbit antibody diluted at 1/8000 in TRIS-BSA buffer and incubated for 1 h at room temperature). After incubation and washing (e.g. 3-5 times with BSA-0.05% Tween blocking solution in TBS buffer), H$_2$O$_2$/tetramethylbenzidine (TMB) substrate indicator solution is added (e.g. 100 µl of TMB substrate for 30 min) to reveal the bound secondary antibody. After incubation at room temperature for 30 minutes, the colorimetric reaction is stopped by the addition of 100 μl 2M H₂SO₄, and the optical density at 405 nm corrected for the absorbance at 650 nm is be measured.

In such competitive ELISA assay, the peptide POSTN fragment contained in the sample (free synthetic peptide used as a standard or the natural peptide fragment comprised in a serum sample) competes with the biotinylated synthetic peptide coated on the microtiter plate for the binding to the primary antibody between. After incubation of a test sample with primary antibodies, the excess of unbound primary antibodies is removed by washing and the amount of a primary antibody remaining on the plate is revealed by the secondary antibody after a colorimetric reaction. The optical density signal in this case is inversely proportional to the concentration of the peptide present in the sample.

The specificity of the antibody used in the ELISA is tested by competition experiments with POSTN fragments generated by recombinant cathepsin K, synthetic peptides of the invention, intact recombinant POSTN and the peptides of the invention wherein one or two amino acids at the C-terminal end are inserted or deleted. This information is used to control that the assay recognizes only the identified cathepsin K cleavage site on POSTN.

Several concentrations of biotinylated peptide, primary and secondary antibodies are used to optimize the signal to noise ratio. Different buffers and incubation conditions (time, temperature) are used to optimize the signal to noise ratio.

Human serum testing is performed to test the peptides of the invention of sequences selected from group of: SEQ ID NO: 2, SEQ ID NO: 3, SEQ ID NO: 4 and SEQ ID NO: 5. To ensure that the ELISA provides accurate and reproducible data, the following controls are performed:
1. Intra and inter assay variability on 3 different pools of serum samples with different concentrations of endogenous peptides of the invention.
2. Linearity using serial dilutions of 3 pools of serum samples.
3. Recovery of various concentrations of synthetic peptides of the invention spiked into 3 pools of human serum.
4. Stability of serum samples at room temperature, 4° C. and after 1 to 4 freeze-thaw cycles.

Example 7

ELISA Assay for a CatK-Digested POSTN Fragment of SEQ ID NO: 2

Detection of presence of peptide 1 which was identified as the main product of the final degradation of human recombinant POSTN by human Cat-K (Examples 2 and 3) is of interest. Therefore, an immunoassay ELISA for the quantitative determination of the presence of peptide 1 in human blood samples was developed as described in Example 6 and as detailed below.

Sample preparation. Venous human blood samples were collected by using standardized blood collection tubes for serum (BD VACUTAINER SST2, advance ref: 367955). Blood was collected between 8 to 10 AM. Subjects were fasting prior to blood collection for at least 8 h or overnight. Shortly after, serum separation by centrifugation is carried out, e.g. 10 min at 3000×g, preferably at 4° C. (2-8° C.) and the obtained serum samples are measured right after. For longer storage aliquot samples were stored at −80° C. in 2 ml micro tube with polypropylene cap (Sarstedt). Samples were not freeze-thaw more than 2 times. Lipemic or hemolysed samples may give erroneous results and were not used. Serums samples were mixed well before assaying (Vortex 10 sec).

ELISA protocol. Microtiter wells were washed 3× with 300 μl of diluted wash buffer (0.5% PBS BSA, Gibco, cell signalling). After final wash, remaining wash buffer was removed by strongly tapping plate against paper towel. Biotinylated synthetic peptides resulting from the biotinylation of peptide 1 (100 μl at 2.5 ng/ml in Tris BSA, coating buffer) were incubated on streptavidin pre-coated microtiter plates (96 wells) for 1 h, tightly covered, at room temperature (RT) (e.g. 18-26° C.) with gentle agitation. After incubation, the solution was removed by aspiration and wells were washed 4× with 300 μl diluted wash buffer, after final wash, remaining wash buffer was removed by strongly tapping plate against paper towel. 50 μl of standard (STD) solution of peptide 1 (see below) or control solution (CTRL) or sample (e.g. serum) was added to the wells. Next, 50 μl of a polyclonal primary antibody to CatK-digested POSTN fragment of SEQ ID NO: 2 (obtained in Example 4) diluted to 1/25000 in assay buffer (TRIS 10 mM, CaCl₂ 10 mM, 0.5% BSA, respectively Sigma, MERCK, Bioconcept Cell Signaling Technology) was added, and the plates were covered and incubated for 19-20 h at 4° C. (2-8° C.) under gentle agitation.

Figure 7:
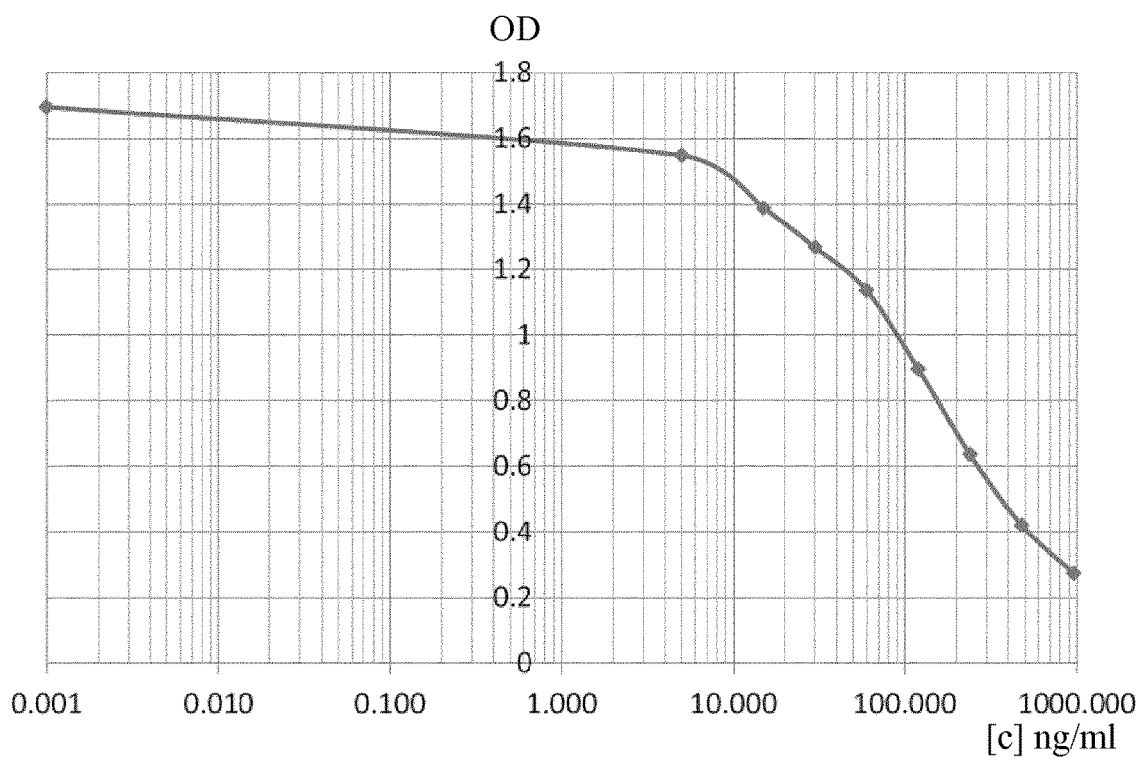
FIG. 7 shows ELISA standard curve (OD at 450 nm versus peptide 1 concentration [c] in ng/ml) as described in Example 7.

Standard (STD) stock solution of peptide 1 at 9.3 mg/ml was diluted with assay buffer to obtain the following individual standard solutions STD 5, 15, 30, 60, 120, 240, 480, 960 ng/ml, STD 0 referred to assay buffer. After incubation, the solution was removed and wells were washed 5× with 300 μl of diluted wash buffer, after final wash remaining wash buffer was removed by strongly tapping plate against paper towel. Next, 100 μl of a secondary anti-rabbit antibody conjugated with horseradish peroxidase (HRP) (peroxydase conjugated affinipure goat anti-rabbit IGG (H+L), Jackson-lab) at concentration 1/150000 was added to the well, the plates were covered tightly and incubated for 1 h at RT under gentle agitation. After incubation, the solution was removed by aspiration and wells were washed 4× with 300 μl diluted wash buffer. 100 μl of a TMB (H₂O₂/tetramethylbenzidine) solution (chromogenic substrate for HRP, Sigma T040) was then added to the wells and incubated in a dark room between 20-30 min (e.g. 25 min) at RT under gentle agitation until the colorimetric reaction was stopped by adding 50 μl of stop solution (H₂SO₄) at concentration 0.2M. The optical density (OD) of all wells on a plate reader was measured immediately after the completion of reactions at 450 nm wavelength. The curve from the OD values of the STD was constructed and the sample concentration was then deduced from the so-obtained standard curve (FIG. 7). The assay was evaluated with 4PL algorithm with various curve fitting methods.

Analytical Sensitivity

The concentration corresponding to OD (STD 0)-3SD (standard deviation) of standard 0 as calculated from 15 repeated measurements of STD 0 was used.

ELISA assay's specificity was analyzed by carrying out the protocol described above using a sample solution further containing peptide 1 or a control peptide 1 of SEQ ID NO: 20 (modified peptide 1 bearing a C-term, threonine), or another control peptide 2 of SEQ ID NO: 21 (fragment of peptide 1 missing the C-term Lysine), or intact POSTN (SEQ ID NO: 1) at concentrations of 60 and 120 ng/ml. The sample with buffer alone was used as a control and OD values were measured as a function of the concentration in target peptide of SEQ ID NO: 2. In another second set of experiments, ELISA assay was performed on a sample with intact recombinant human POSTN, or on a sample wherein recombinant human POSTN was digested by recombinant CatK for 4 hours at a molar ratio of 1/10. A buffer used for digestion reaction was used as a negative control.

Analytical Reproducibility

Intra-assay variability was assessed on 4 serum samples of different peptide concentrations run 10-12 times in the same assay. Inter-assay variability was assessed on 3 serum samples were run 4-10 times in different assays. The coefficient of variability (CV) was calculated by dividing the SD of the measurements with the mean value of each sample. In general, intra-assay and inter assay % CV of less than 15 are acceptable.

Assay Linearity 2 serum samples with high concentrations of endogenous peptide 1 were serially diluted in the assay buffer. The mean % recovery was then calculated by dividing the measured concentration by the expected value taking into account the dilution factor. Recoveries ranging from 80 to 120% are considered acceptable for such ELISA technology.

The obtained standard curve for peptide 1 is consistent with standard curves provided by final release quality control (QC) protocols (OD values of 1.40 or higher obtained for the zero standard). The analytical lower limit of detection (LLOD) for this ELISA assay was estimated to be 9.1 ng/ml. It was estimated using the concentration of the target peptide corresponding to the OD value of the 0 standard-3 SD. The Lower Limit of Quantification (LLOQ) was estimated to be 12 ng/ml. The LLOQ is the concentration of the target peptide in serum samples that can be measured with a % CV below 20%.

Figure 8:
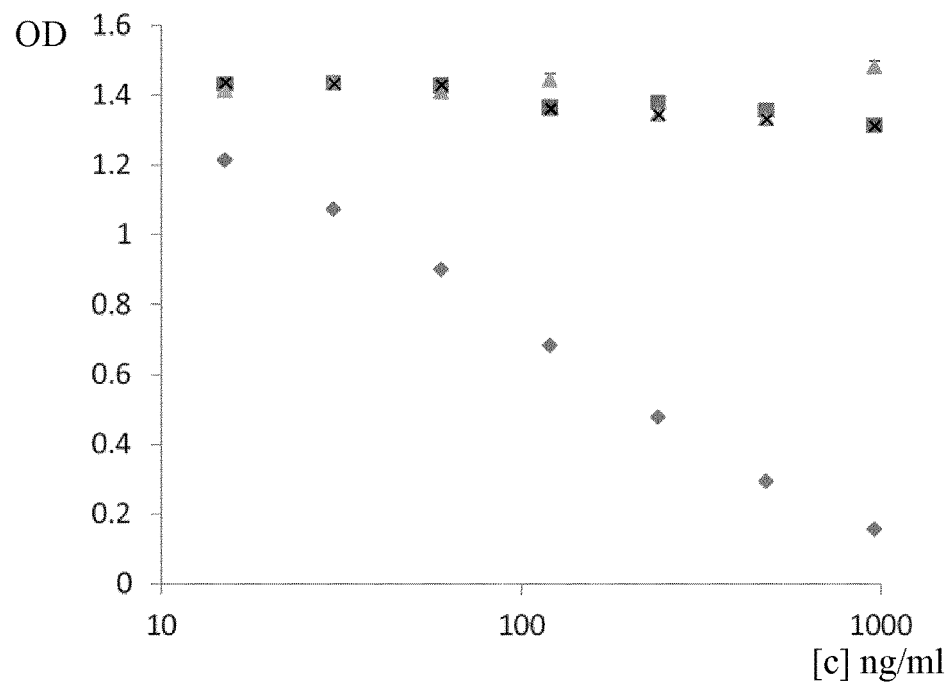
FIG. 8 shows ELISA test read out (OD at 450 nm versus peptide concentration [c] in ng/ml) described in Example 7 for peptide 1 (rhombus), control peptide of SEQ ID NO: 20 (square), control peptide of SEQ ID NO: 21 (triangle) and POSTN (SEQ ID NO: 1, cross).

The specificity of this ELISA assay was supported since it did not detect control peptide SEQ ID NO: 20, control peptide of SEQ ID NO: 21 nor intact POSTN of SEQ ID NO: 1 at the tested concentrations and was only sensitive for peptide 1 (FIG. 8). In the second set of experiments, intact recombinant human POSTN (concentration of 0.04 µg/µl) was not detected by ELISA but in contrast, in a sample where intact POSTN was digested by CatK, CatK-digested POSTN fragment of SEQ ID NO: 2 was detected at concentration of 29 ng/ml. The intra-assay CV was below 12.5% and the inter-assay CV for serum sample above the LLOQ (i.e. 12 ng/ml) was below 14 (Table 2).

TABLE 2

| Mean concentration (ng/ml) | N | CV % |
|---|---|---|
| intra-assay | | |
| 32.7 | 10 | 8.0 |
| 50.8 | 10 | 9.1 |
| 132.9 | 10 | 12.4 |
| 201 | 12 | 11.7 |
| inter-assay | | |
| 7.5 | 8 | 17.1 |
| 27.2 | 10 | 13.8 |
| 42.8 | 4 | 10.6 |

TABLE 3

| Serum ID | Dilution | Peptide of SEQ ID NO: 2 (ng/ml) | % recovery |
|---|---|---|---|
| I | Neat (high natural concentration) | 201 | |
| | ½ | 104 | 103 |
| | ¼ | 55.1 | 110 |
| | ⅛ | 31.1 | 124 |
| II | Neat (high natural concentration) | 314 | |
| | ½ | 187 | 119 |
| | ¼ | 84 | 107 |
| | ⅛ | 39 | 99 |

Those data support that competitive ELISA assay according to the invention can reliably and specifically detect peptide 1 in human serum samples.

Example 8

Presence of CatK-Digested POSTN Fragment of SEQ ID NO: 2 in a Population of Retired Subjects The presence of peptide 1 was measured with an ELISA assay of the invention as described in Example 7. The serum of 195 randomly chosen subjects of the Geneva Retiree Cohort (GERICO) comprising more than 1'000 subjects (¾ females) from the general population with a mean age of 65.0±1.40 years for 160 women and 35 men was collected and assayed.

Statistical Analysis

Statistical analyses were performed using MedCalc Statistical Software version 13.1.2 (MedCalc Software bvba, Ostend, Belgium). All data were reported as means±SD. Normal distribution was evaluated by d'Agostino-Pearson test. To take into account that not all variables were normally distributed, the differences were assessed by a Mann-Whitney U test. A one way ANOVA with the tertiles of periostin fragment serum levels (peptide 1) employed as a factor was performed. Correlations of bone microstructure and peptide 1 serum levels with bone parameters were analyzed by single and multivariate linear regression analyses. $P<0.05$ was considered the level of statistical significance for regression coefficient (or β values).

The measured mean concentration of the peptide 1 in those subjects' serum was at 38.8 ng/ml with respectively the lowest and highest value of 10.9 and 170.3 ng/ml as shown in Table 4 below. Peptide concentration value did significantly differ between men and women and is not correlated to age. Table 5 shows the distribution of peptide 1 concentrations among the subject's population.

TABLE 4

| | |
|---|---|
| Sample size | 195 |
| Lowest value | 10.93 |
| Highest value | 170.29 |
| Arithmetic mean | 38.7869 |
| 95% CI for the mean | 35.9592 to 41.6147 |
| Median | 35.1500 |
| 95% CI for the median | 32.3065 to 37.0204 |
| Variance | 400.8466 |
| Standard deviation | 20.0212 |
| Relative standard deviation | 0.5162 (51.62%) |
| Standard error of the mean | 1.4337 |
| Coefficient of Skewness | 2.4346 (P < 0.0001) |
| Coefficient of Kurtosis | 11.0284 (P < 0.0001) |
| D'Agostino-Pearson test for Normal distribution | reject Normality (P < 0.0001) |

TABLE 5

| Percentiles | Peptide 1 (ng/ml) | 95% CI |
| --- | --- | --- |
| 2.5 | 13.0462 | 11.5298 to 14.4720 |
| 5 | 14.8700 | 13.0200 to 19.4620 |
| 10 | 20.2800 | 16.7141 to 22.8331 |
| 25 | 25.7150 | 24.5058 to 27.7527 |
| 75 | 47.6775 | 41.9709 to 52.2508 |
| 90 | 61.4100 | 56.5904 to 65.0074 |
| 95 | 67.8150 | 63.5783 to 86.5678 |
| 97.5 | 85.0588 | 68.0309 to 143.5525 |

Figure 9:
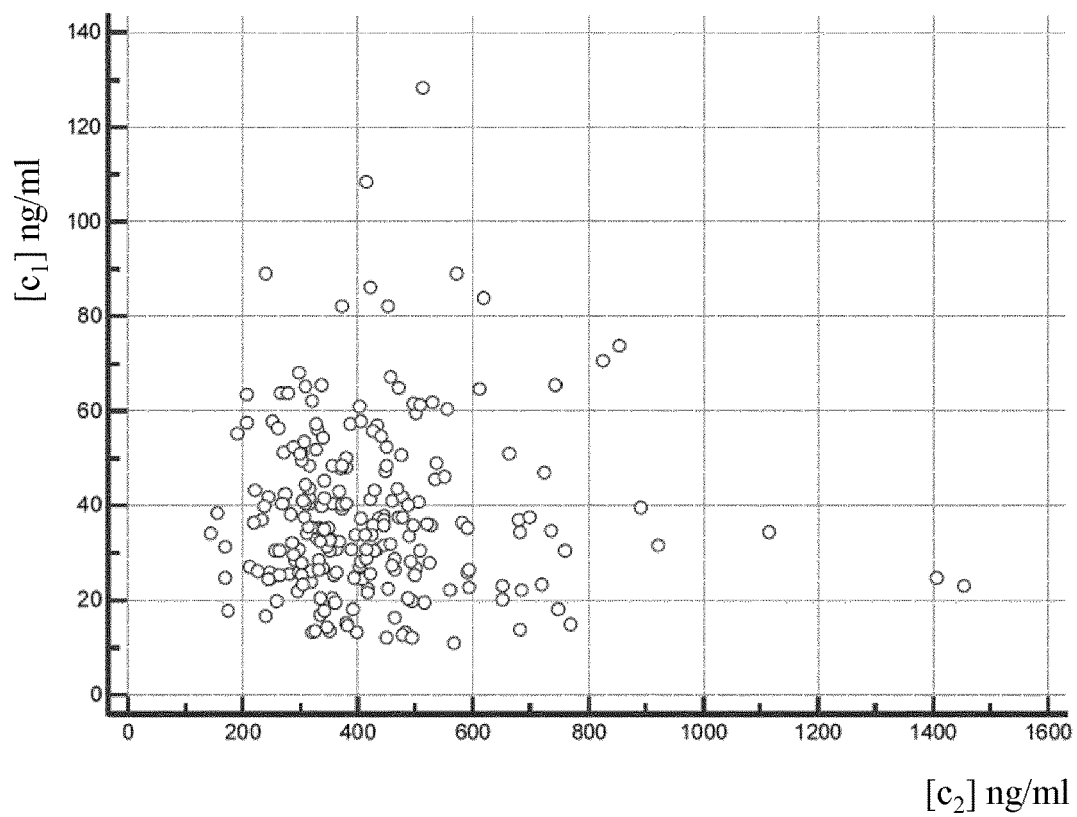
FIG. 9 represents serum levels of peptide 1 $[c_i]$ versus sPOSTN serum levels $[c_2]$ (ng/ml) measured in Example 8.

The amount of the peptide in tested serum was not associated with total POSTN (FIG. 9) nor with the POSTN measured by POSTN antibodies from USCN or Biomedica (FIG. 12).

Those data support that an ELISA assay of the invention is capable of detecting CatK-digested POSTN fragment of SEQ ID NO: 2 in general population sera with sensitivity to gender population which is indicative of a potential sensitivity to the bone quality status.

Example 9

CatK-Digested POSTN Fragment of SEQ ID NO: 2 as Specific Marker of Cortical Bone Compartment Various bone markers and bone structure characteristics were measured in the patients as selected in patients' population of Example 8 as follows:

CTX (cross-linked C-terminal telopeptide of type I collagen) and P1NP (procollagen type 1 N-terminal propeptide) are used as markers of the bone resorption and of the bone formation, respectively were measured on a Cobas-6000 instrument using Elecsys reagents (Roche diagnostics). Serum POSTN (sPOSTN) level was measured by ELISA assay (SEH339Hu, USCN, China).

Bone mineral density (BMD) of the femoral neck was determined by dual-energy x-ray absorptiometry (DXA) using a Hologic QDR Discovery instrument. High-resolution peripheral quantitative computed tomography measurements were performed using an XtremeCT instrument (Scanco Medical AG, Basserdorf Switzerland). Scanning of the immobilized non-dominant forearm and distal tibia was performed as previously described (Durosier et al., 2013, *J Clin Endocrinol Metab*, 98(9): 3873-83). Shortly, a stack of 110 computed tomography (CT) slices was acquired over a 9-mm length with an isotropic voxel size of 82 mm, starting proximally at 9.5 and 22.5 mm from a joint margin reference line for distal radius and distal tibia, respectively. Reproducibility assessed with repositioning was 0.6-1.0% and 2.8-4.9% for density variables and trabecular (Tb.) and cortical (Ct.) microstructures, respectively. Tb. and Ct. microstructure parameters (Bone volume on total volume (BV/TV), Tb. or Ct. area (Tb./Ct.Ar), Tb. or Ct. thickness (Ct.Th), Moment of Inertia (MI) and porosity were evaluated as previously described (Chevalley et al., 2013, *Bone*, 55(2): 377-83).

Cross sectional (Tables 6) analyses were carried out to determine whether this peptide could be an independent and specific marker of cortical bone compartment.

Correlations of peptide 1 and sPOSTN with bone parameters were analyzed as described in Example 8. All data were reported as means+/−SD. To take into account that not all variables were normally distributed, the differences were assessed by a d'Agostino-Pearson test. CTX adjustment of the measured levels of peptide 1 was performed by covariance in order to demonstrate that the association of periostin with bone structure is independent of classical bone turnover markers such as CTX.

TABLE 6

| | peptide 1 | sPOSTN | peptide 1 sPOSTN | peptide 1* | sPOSTN* | peptide 1*/ sPOSTN* |
| --- | --- | --- | --- | --- | --- | --- |
| Age (years) | 0.09 (p = 0.19) | 0.002 (p = 0.96) | 0.06 (p = 0.44) | 0.09 (p = 0.21) | −0.005 (p = 0.93) | 0.05 (p = 0.48) |
| CTX (ng/l) | −0.09 (p = 0.20) | −0.08 (p = 0.17) | −0.06 (p = 0.39) | — | — | — |
| P1NP (µg/l) | −0.04 (p = 0.55) | −0.03 (p = 0.57) | −0.03 (p = 0.65) | 0.07 (p = 0.35) | 0.05 (p = 0.41) | 0.04 (p = 0.60) |
| Peptide 1 (ng/ml) | — | −0.01 (p = 0.81) | 0.77 (p < 0.0001) | — | −0.01 (p = 0.87) | 0.76 (p < 0.0001) |
| sPOSTN (ng/ml) | −0.01 (p = 0.84) | — | −0.50 (p < 0.0001) | −0.02 (p = 0.80) | — | −0.50 (p < 0.0001) |
| BMD neck (g/cm$^2$) | 0.06 (p = 0.41) | 0.09 (p = 0.15) | −0.05 (p = 0.50) | 0.04 (p = 0.60) | 0.08 (p = 0.21) | −0.07 (p = 0.35) |
| BV/TV tibia | −0.008 (p = 0.91) | 0.10 (p = 0.11) | −0.11 (p = 0.13) | −0.03 (p = 0.70) | 0.10 (p = 0.11) | −0.13 (p = 0.08) |
| Tb. vBMD (mgHA/cm$^3$) | −0.008 (p = 0.91) | 0.12 (p = 0.06) | −0.11 (p = 0.13) | −0.34 (p = 0.70) | 0.10 (p = 0.11) | −0.13 (p = 0.08) |
| Ct. area tibia (mm$^2$) | −0.14 (p = 0.05) | 0.26 (p < 0.001) | −0.24 (p = 0.0008) | −0.18 (p = 0.01) | 0.25 (p > 0.0001) | −0.28 (p = 0.0002) |
| Ct. vBMD (mgHA/cm$^3$) | −0.08 (p = 0.12) | 0.16 (p = 0.01) | −0.14 (p = 0.05) | −0.14 (p = 0.05) | 0.14 (p = 0.03) | −0.17 (p = 0.02) |
| Ct. Porosity (%) tibia | −0.07 (p = 0.36) | −0.02 (p = 0.70) | −0.03 (p = 0.70) | −0.05 (p = 0.51) | −0.005 (p = 0.93) | −0.01 (p = 0.83) |
| Total polar MI (mm$^4$) | −0.11 (p = 0.11) | 0.27 (p < 0.001) | −0.24 (p = 0.0008) | −0.14 (p = 0.05) | 0.26 (p = 0.001) | −0.27 (p = 0.0003) |
| Failure load tibia (N) | −0.07 (p = 0.33) | 0.24 (p < 0.01) | −0.21 (p = 0.004) | −0.10 (p = 0.17) | 0.23 (p = 0.0003) | −0.23 (p = 0.001) |
| Stiffness tibia | −0.07 (p = 0.35) | 0.24 (p < 0.0001) | −0.20 (p = 0.005) | −0.10 (p = 0.18) | 0.23 (p = 0.0004) | −0.23 (p = 0.001) |

Figure 10:
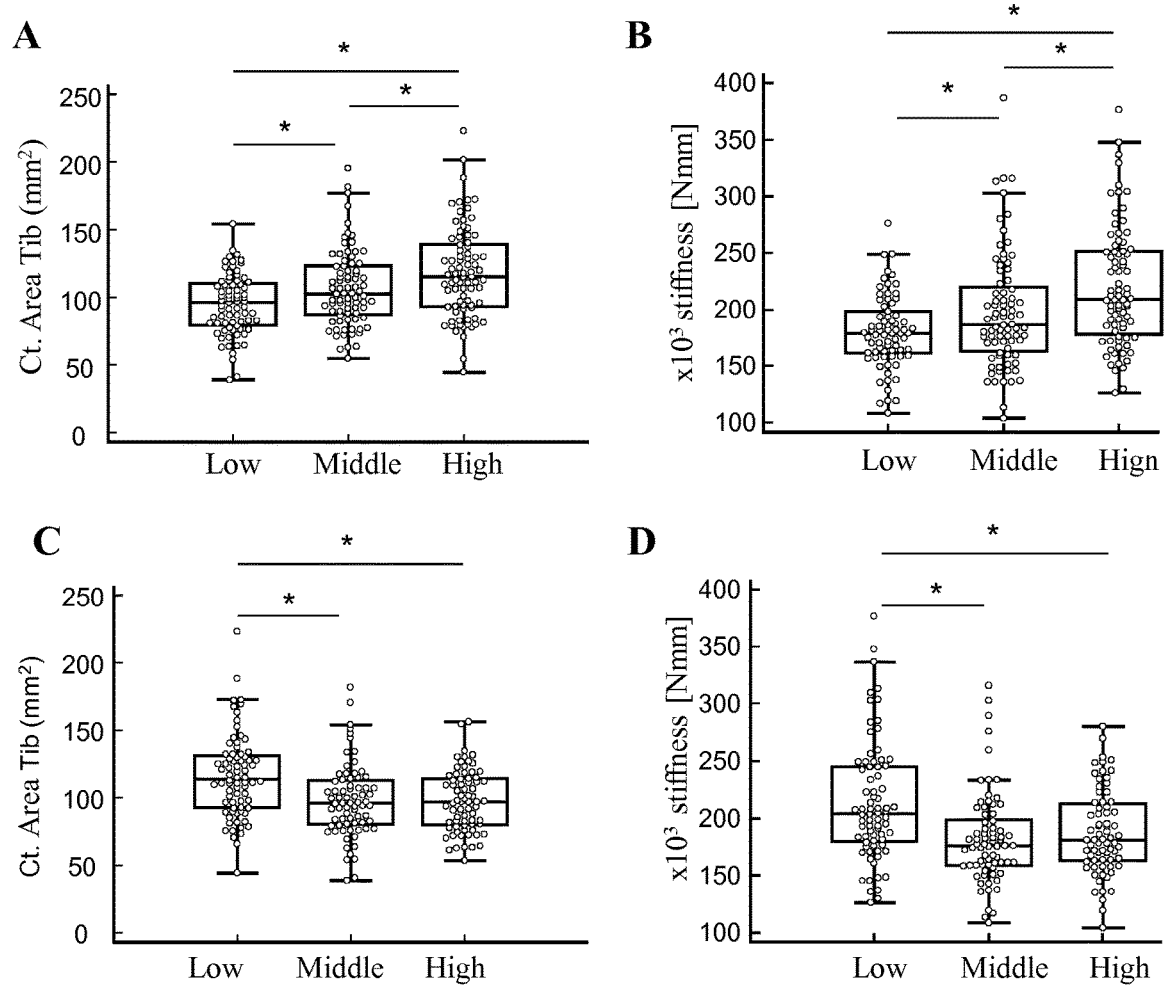
FIG. 10 shows tibia Ct. area and stiffness distribution of low, middle and high tertile of sPOSTN (A, B) and Peptide 1 to sPOSTN ratio (C, D) as described in Example 9.

*CTX adjustment sPOSTN was positively correlated with cortical area, Ct. vBMD and fine element analysis parameters (total polar MI, failure load and stiffness) and not associated with BMD or bone turnover markers (CTX, P1NP) (Tables 6) which are known markers for bone parameters but not specific for the cortical bone. Peptide 1 was negatively associated with cortical parameters (Ct. area tibia, Ct. vBMD, total polar MI) and not trabecular parameters (Tb. vBMD) confirming the association of periostin with the cortical compartment. Peptide 1 to sPOSTN ratio, i.e. an index of the digested periostin was negatively correlated with cortical area, Ct. vBMD, M, failure load and stiffness and total polar MI. These negative associations remain significant after adjustment by CTX, indicating that peptide 1 measurement gives additional information than bone remodeling markers (Table 6). Further, subjects on the high tertile of sPOSTN have high cortical area and stiffness whereas high tertile Peptide 1 to sPOSTN ratio have significantly lower cortical area and stiffness (FIG. 10).

Together, the above data indicate that CatK-digested POSTN fragment of SEQ ID NO: 2 is a specific marker of cortical bone compartment that provides additional information to known biochemical markers of bone turnover (CTX, P1NP).

Example 10

CatK-Digested POSTN Fragment of SEQ ID NO: 2 as Specific Marker of Cortical Bone Compartment (Prospective Analysis)

A prospective analysis of bone markers and parameters as well as serum levels of peptide 1 and POSTN was carried out on 137 randomly chosen subjects of the GERICO population as described above. In this study, bone microstructure measurements (DXA, HRpQCT) were performed 3 years after the evaluation of bone markers in order to determine if bone markers are predictive of bone structure. BMD and tibial bone microarchitecture regression are reported in Table 7 as monitored with Peptide 1, sPostn and ratio Peptide 1 to sPostn.

TABLE 7

|  | Peptide 1 | sPOSTN | Peptide 1/ sPOSTN |
| --- | --- | --- | --- |
| Age (years) | 0.11 (p = 0.18) | 0.03 (p = 0.70) | 0.02 (p = 0.84) |
| BMD neck (g/cm$^2$) | 0.03 (p = 0.70) | 0.10 (p = 0.19) | −0.09 (p = 0.25) |
| BV/TV tibia | −0.04 (p = 0.61) | 0.16 (p = 0.03) | −0.12 (p = 0.15) |
| BV/TV radius | −0.07 (p = 0.41) | 0.20 (p = 0.01) | −0.11 (p = 0.19) |
| Ct. area tibia (mm$^2$) | −0.14 (p = 0.10) | 0.30 (p < 0.001) | −0.23 (p < 0.01) |
| Ct. area radius (mm$^2$) | −0.11 (p = 0.23) | 0.28 (p < 0.001) | −0.24 (p = 0.006) |
| Ct.Th tibia (mm$^2$) | −0.14 (p = 0.10) | 0.21 (p < 0.01) | −0.20 (p = 0.02) |
| Ct.Th radius (mm$^2$) | −0.11 (p = 0.21) | 0.20 (p = 0.01) | −0.16 (p = 0.06) | sPOSTN was positively correlated BV/TV, Ct. area and CtTh of tibia and radius and not associated with BMD (Table 7). Peptide 1 was negatively associated with cortical parameters (Ct. area, CtTh). Peptide 1 to sPOSTN ratio was negatively correlated with Ct. area and CTTH of tibia and radius confirming that CatK-digested POSTN fragment of SEQ ID NO: 2 is a specific marker of cortical bone. The same analysis is then performed 6 years after the initial evaluation of bone markers on the cohort of 1'000 subjects.

Example 11

Association of CatK-Digested POSTN Fragment of SEQ ID NO: 2 with Cortical Bone Compartment are Maintained After Adjustment for POSTN (Prospective Analysis)

Bone markers and bone structure parameters are analyzed together with serum levels of peptide 1 and POSTN measured with commercially available kits (with two commercially available kits: ELISA Kit for Periostin, Uscn Life Science, Inc. (Product No.: SEH339Hu) (Kit 1), and ELISA Kit for Periostin, Biomedica Immunoassays (Cat. No.: BI-20433) (Kit 2) on 165 randomly chosen subjects of the GERICO population as described above. The measured levels of peptide 1 were adjusted by multiple regression analysis with POSTN level as detected with kit 1 or kit 2. BMD and bone microarchitecture regression with peptide 1 and peptide 1 adjusted (adj.) to POSTN levels measured by kit 1 or 2 are reported in Table 8.

TABLE 8

|  | peptide 1 | peptide 1 - adj. POSTN (kit 1) | peptide 1 - adj. POSTN (kit 2) |
| --- | --- | --- | --- |
| Age (years) | 0.06 p = 0.47 | −0.01 p = 0.90 | 0.06 p = 0.47 |
| BMD neck (g/cm$^2$) | −0.02 p = 0.78 | −0.09 p = 0.26 | −0.01 p = 0.87 |
| BV/TV tibia | −0.07 p = 0.35 | −0.12 p = 0.11 | −0.07 p = 0.39 |
| BV/TV radius | −0.06 p = 0.44 | −0.07 p = 0.36 | −0.07 p = 0.41 |
| Ct. area tibia (mm$^2$) | −0.17 p = 0.02 | −0.19 p = 0.02 | −0.16 p = 0.04 |
| Ct. area radius (mm$^2$) | −0.14 p = 0.10 | −0.16 p = 0.05 | −0.11 p = 0.16 |
| Ct.Th tibia (mm$^2$) | −0.16 p = 0.03 | −0.15 p = 0.05 | −0.15 p = 0.09 |
| Ct.Th radius (mm$^2$) | −0.16 p = 0.05 | −0.16 p = 0.05 | −0.15 p = 0.11 |

Peptide 1 (SEQ ID NO: 2) was negatively associated with cortical parameters (Ct. area tibia, CtTh tibia/radius) and at least for Ct. area tibia this association remained negative after adjustment of Peptide 1 level to the POSTN level measured by two different kits. For CtTh tibia/radius negative association for Peptide 1 remained after adjustment of Peptide 1 level to the POSTN level measured by kit 1. Also, after adjustment of Peptide 1 level to the POSTN level measured by kit 1 negative association of Peptide 1 for Ct. radius become statistically significant.

Figure 11:
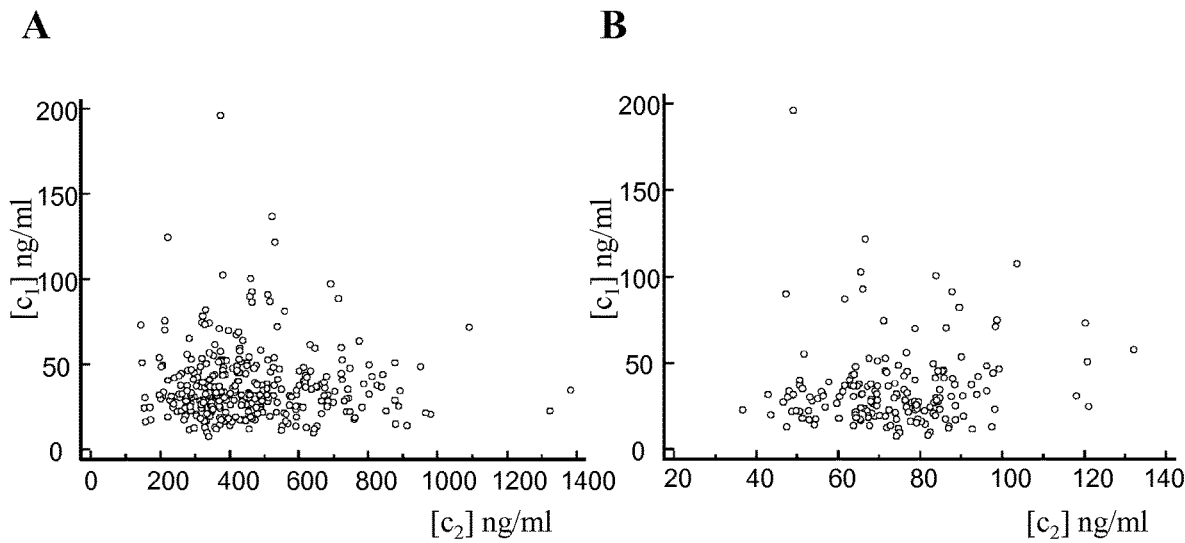
FIG. 11 represents serum levels of peptide 1 $[c_1]$ versus sPOSTN serum levels $[c_2]$ in ng/ml measured with commercial kits 1 (A, n=324) or 2 (B, n=176) as described in Example 11.

The amount of peptide 1 in tested sera was not associated with total POSTN as measured by kit 1 or 2 (FIG. 11).

This result confirms that developed antibodies used for the detection of CatK-digested POSTN fragment of the invention in a serum do not detect the same molecules as the commercial antibodies and thus are specific. Further, CatK-digested POSTN fragment of the invention can serve as a specific marker of cortical bone compartment.

Example 12

Association of CatK-Digested POSTN Fragment of SEQ ID NO: 2 with Incident Fracture (Prospective Analysis)

An analysis of bone markers and parameters as well as serum levels of peptide 1 and POSTN were carried out on subjects with incident fracture and matched controls.

In this study, within GERICO cohort of 759 post-menopausal women that were followed up to 6 years, 54 incident fracture with low and middle trauma (osteoporotic fracture; "fracture" group) were registered (excluding vertebral, toe, finger and skull fractures) and compared to matched for age and body mass index (BMI) randomly selected subjects from GERICO (n=198, "non-fracture" group). An analysis of bone markers and parameters as well as serum levels of peptide 1 and POSTN was carried out as described in Example 9. POSTN was measured with ELISA Kit for Periostin, Uscn Life Science, Inc. (Product No.: SEH339Hu). In order to quantify how strongly Peptide 1 levels were associated with the presence or absence of fracture the Odds ratio based on 1 SD of peptide 1 was calculated. Cox model proportional hazard regression and area under the curve (AUC) of Receiver Operating Characteristic (ROC) curve was performed as statistic survival model using MedCalc Statistical Software version 13.1.2. Survival models relate the time that passes before some event occurs, here the risk of fracture, to one or more covariates that may be associated with that quantity of time.

The fracture risk assessment tool (FRAX) developed by the World Health Organization (see Worldwide Website: shef.ac.uk/FRAX/) and country-specific data (Lippuner et al., 2010, *Osteoporosis Int.* 21: 381-9) was used to assess subjects' risk of fracture using clinical risk factors such as age, BMI and history of fracture with inclusion of femoral neck BMD.

Characteristic of the cohort is reported in Table 9 and shows that the fracture group had lower values of BMD, Tb. and Ct. microstructure parameters at the tibia and radius (BV/TV, Ct. area, Ct.Th). Peptide 1 level was significantly higher in the fracture group versus control group (+53%, p<0.001), whereas the classical bone turnover markers (CTX, P1NP) and the total POSTN were not significantly different between the two groups.

TABLE 9

|  | Fracture | Non fracture | P value |
| --- | --- | --- | --- |
| Age (years) | 65.2 ± 1.4 | 65.0 ± 1.4 | 0.19 |
| BMI | 25.2 ± 4.6 | 25.0 ± 4.1 | 0.81 |
| BMD neck (g/cm$^2$) | 0.6764 ± 0.11 | 0.7245 ± 0.11 | 0.004 |
| BV/TV tibia | 0.117 ± 0.03 | 0.127 ± 0.03 | 0.01 |
| BV/TV radius | 0.103 ± 0.03 | 0.119 ± 0.029 | 0.001 |
| Ct. area tibia (mm$^2$) | 87.70 ± 23.13 | 106.54 ± 28.37 | 0.001 |
| Ct. area radius (mm$^2$) | 43.82 ± 12.19 | 54.20 ± 13.74 | <0.001 |
| Ct.Th tibia (mm$^2$) | 0.8442 ± 0.25 | 1.007 ± 0.25 | <0.001 |
| Ct.Th radius (mm$^2$) | 0.6432 ± 0.196 | 0.7682 ± 0.1681 | <0.001 |
| Ct. Porosity (%) tibia | 0.094 ± 0.037 | 0.082 ± 0.03 | 0.01 |
| Ct. Porosity (%) radius | 0.028 ± 0.01 | 0.026 ± 0.01 | 0.35 |
| CTX (ng/L) | 383.17 ± 202 | 362.43 ± 216 | 0.51 |
| P1NP (ug/L) | 45.94 ± 21.14 | 46.62 ± 25.43 | 0.56 |
| POSTN (ng/ml) | 431.88 ± 191 | 412 ± 165 | 0.52 |
| Peptide 1 (ng/ml) | 63.30 ± 42.37 | 41.38 ± 25.84 | <0.001 |

Cox proportional hazard regression was obtained as reported in Table 10 and showed a positive association of Peptide 1 and incident fracture with a hazard ratio of 1.58 [1.24-2.01] indicating that with an increase of 1 standard deviation of peptide 1, one increased risk of fracture by 58% (Table 10 A). Furthermore, with the highest tertiles of Peptide 1 the risk of fracture was further increased with a hazard ratio of 4.74 [2.16-10.40]. Predictions of fracture by Peptide 1 remained significant after adjustment by BMD neck, Ct. area radius, BV/TV radius or CTX marker (Table 10 B-E).

TABLE 10

|  | Hazard ratio | P value |
| --- | --- | --- |
| A. Cox Hazard ratio (Independent) | | |
| Peptide 1 (ng/ml) | 1.58 [1.24-2.01] | 0.001 |
| BMD neck (g/cm2) | 0.72 [0.54-0.96] | P < 0.01 |
| CTX (ng/L) | 0.97 [0.92-1.03] | 0.39 |
| B. Cox Hazard ratio (model) | | |
| Peptide 1 (ng/ml) | 1.62 [1.27-2.07] | P < 0.001 |
| BMD neck (g/cm2) | 0.72 [0.54-0.97] | P < 0.01 |
| C. Cox Hazard ratio (model) | | |
| Peptide 1 (ng/ml) | 1.58 [1.23-2.02] | P < 0.001 |
| Ct. area radius | 0.45 [0.32-0.64] | P < 0.001 |
| D. Cox Hazard ratio (model) | | |
| Peptide 1 (ng/ml) | 1.54 [1.20-1.95] | P < 0.001 |
| BV/TV radius | 0.98 [0.98-0.99] | P < 0.05 |
| E. Cox Hazard ratio (model) | | |
| Peptide 1 (ng/ml) | 1.59 [1.24-2.02] | P < 0.001 |
| CTX (ng/L) | 1.006 [0.95-1.06] | P < 0.01 |

The ROC curve illustrates the true positive rate (Sensitivity) in function of the false positive rate (1-Specificity) for different cut-off points and thus allows appreciating how well a parameter can distinguish between fracture and non-fracture group by measuring the area under the curve (AUC). Individually, Peptide 1 as well as standard clinical measures such as BMD and FRAX significantly discriminated fracture events (Table 11). However, peptide 1 combined with BMD and peptide 1 combined with FRAX discriminated more subjects with fracture than BMD or FRAX alone (FIG. 11).

TABLE 11

| ROC | Odds ratio | AUC | P value |
| --- | --- | --- | --- |
| Peptide 1 (ng/ml) | 1.76 [1.27-2.43] | 0.6771 | 0.001 |
| BMD neck (g/cm$^2$) | 0.15 [0.02-1.28] | 0.5548 | P = 0.08 |
| FRAX | 2.23 × 10$^{-7}$ [2.16 × 10$^{-11}$-0.0002] | 0.6668 | 0.001 |

This result confirms that developed antibodies used for the detection of CatK-digested POSTN fragment of the invention in a serum can be used as an additional tool to identify patients which at risk of getting an osteoporotic fracture. This higher association of CatK-digested POSTN fragment of the invention with incident fracture as compared to the cortical structure parameters indicates that CatK-digested POSTN fragment of the invention do not only serves as a marker of bone structure but also as a marker of bone quality.

LIST OF SEQUENCES

*Homo sapiens* periostin

SEQ ID NO: 1
MIPFLPMFSLLLLLIVNPINANNHYDKILAHSRIRGRDQGPNVCALQQI

LGIKKKYFSICKNWYKKSICGQKTIVLYECCPGYMRMEGMKGCPAVLPI

DHVYGILGIVGATTIQRYSDASKLREEIEGKGSFTYFAPSNEAWDNLDS

DIRRGLESNVNVELLNALHSHMINKRMLIKDLKNGMIIPSMYNNLGLFI

NHYPNGVVIVNCARIIHGNQIAINGVVHVIDRVLIQIGTSIQDFIEAED
DLSSFRAAAITSDILEALGRDGHFILFAPTNEAFEKLPRGVLERIMGDK
VASEALMKYHILNTLQCSESIMGGAVFETLEGNTIEIGCDGDSITVNGI
KMVNKKDIVINNGVIHLIDQVLIPDSAKQVIELAGKQQTTFIDLVAQLG
LASALRPDGEYILLAPVNNAFSDDILSMDQRLLKLILQNHILKVKVGLN
ELYNGQILETIGGKQLRVFVYRTAVCIENSCMEKGSKQGRNGAIHIFRE
IIKPAEKSLHEKLKQDKRFSTFLSLLEAADLKELLTQPGDWILFVPIND
AFKGMTSEEKEILIRDKNALQNIILYHLTPGVFIGKGFEPGVINILKTI
QGSKIFLKEVNDILLVNELKSKESDIMTINGVIHVVDKLLYPADTPVGN
DQLLEILNKLIKYIQIKFVRGSTFKEIPVIVYTTKIITKVVEPKIKVIE
GSLQPIIKTEGPTLIKVKIEGEPEFRLIKEGETITEVIHGEPIIKKYTK
IIDGVPVEITEKETREERIITGPEIKYTRISIGGGETEETLKKLLQEEV
IKVIKFIEGGDGHLFEDEEIKRLLQGDTPVRKLQANKKVQGSRRRLREG
RSQ

Peptide 1 (Periostin fragment 1)
SEQ ID NO: 2
GSLQPIIK

Peptide 2 (Periostin fragment 2)
SEQ ID NO: 3
EEIEGKGSFT

Peptide 3 (Periostin fragment 3)
SEQ ID NO: 4
TTQGSKIF

Peptide 4 (Periostin fragment 4)
SEQ ID NO: 5
NEAFEKLPR

Peptide 5 (Periostin fragment 5)
SEQ ID NO: 6
GSLQPIIKTEGPT

Peptide 6 (Periostin fragment 6)
SEQ ID NO: 7
SEEKEILIR

Peptide 7 (Periostin fragment 7)
SEQ ID NO: 8
AADLKELL

Peptide 8 (Periostin fragment 8)
SEQ ID NO: 9
TGGGETEETLK

Peptide 9 (Periostin fragment 9)
SEQ ID NO: 10
TTQGSKIFL

Peptide 10 (Periostin fragment 10)
SEQ ID NO: 11
SALRPDGEYTLL

Peptide 11 (Periostin fragment 11)
SEQ ID NO: 12
EGETITEVIHGEPIIK

Peptide 12 (Periostin fragment 12)
SEQ ID NO: 13
YECCPGYMR

Peptide 13 (Periostin fragment 13)
SEQ ID NO: 14
AADLKELLT

Peptide 14 (Periostin fragment 14)
SEQ ID NO: 15
IGCDGDSITVNGIK

Peptide 15 (Periostin fragment 15)
SEQ ID NO: 16
NDAFKGMT

Peptide 16 (Periostin fragment 16)
SEQ ID NO: 17
AEDDLSSFR

Peptide 17 (Periostin fragment 17)
SEQ ID NO: 18
DTLLVNELK

*Homo sapiens* CatK (AAH16058.1)
SEQ ID NO: 19
Mwglkvlllpvvsfalypeeildthwelwkkthrkgynnkvdeisrrli
weknlkyisihnleaslgvhtyelamnhlgdmtseevvqkmtglkvpls
hsrsndtlyipewegrapdsvdyrkkgyvtpvknqgqcgscwafssvga
legglkkktgkllnlspqnlvdcvsendgcgggymtnafgyvqknrgid
sedaypyvggeescmynptgkaakorgyreipegnekalkravarvgpv
svaidasltsfqfyskgvyydescnsdnlnhavlavgygiqkgnkhwii
knswgenwgnkgyilmarnknnacgianlasfpkm Control Peptide 1,
SEQ ID NO: 20
GSLQPIIKT Control Peptide 2,
SEQ ID NO: 21
GSLQPII Peptide 18 (Periostin fragment 18)
SEQ ID NO: 22
INGVVHVIDRVLT Peptide 19 (Periostin fragment 19)
SEQ ID NO: 23
TSIQDFIEAEDDLSSFR Peptide 20 (Periostin fragment 20)
SEQ ID NO: 24
ATTTQRYSDASKLR Peptide 21 (Periostin fragment 21)
SEQ ID NO: 25
APTNEAFEKLPR

The invention claimed is:

1. An isolated periostin (POSTN) fragment consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or variants thereof, wherein said variant has one or more amino acid that is deleted or is a conservative substitution.

2. The POSTN fragment according to claim 1, said POSTN fragment consisting of SEQ ID NO: 2, SEQ ID NO: 3, SEQ ID NO: 4, SEQ ID NO: 5, or a variant thereof.

3. The POSTN fragment according to claim 1, said POSTN fragment consisting of SEQ ID NO: 2.

4. A method for detecting a POSTN fragment from a biological fluid sample of a mammalian subject comprising the steps of:
   (a) providing a biological fluid sample obtained from a mammalian subject;
   (b) providing a solid support having bound thereto at least one POSTN fragments according to claim 1;
   (c) bringing said solid support into contact with said biological fluid sample;
   (d) bringing said solid support into contact with at least one antibody specific for said POSTN fragment, wherein the contacting is under conditions sufficient for binding of said POSTN fragment present in said biological fluid sample to said at least one antibody through antigen-antibody interactions;
(e) washing the solid matrix for removing any unbound antibody from the surface of the said solid matrix; and
(f) detecting the presence of an antigen-antibody complex bound to the said solid matrix, wherein the presence of the said complex is indicative that the biological fluid sample contains one or more POSTN fragment.

5. A method for detecting a POSTN fragment in a biological fluid sample of a mammalian subject comprising the steps of:
(a) providing a biological fluid sample obtained from a mammalian subject;
(b) bringing said biological fluid sample into contact with a solid matrix where at least one antibody is bound to, wherein said at least one antibody is specific for a POSTN fragment according to claim 1, and wherein the contacting is under conditions sufficient for binding a POSTN fragment present in the said biological fluid sample to said at least one antibody through antigen-antibody interactions;
(c) removing the biological fluid sample from the solid matrix for removing any unbound material from the surface of the said solid matrix; and
(d) detecting the presence of an antigen-antibody complex bound to said solid matrix, wherein the presence of the said complex is indicative that the biological fluid sample contains one or more POSTN fragment(s).

6. The method according to claim 4, wherein the said at least one antibody is specific for a POSTN fragment consisting of SEQ ID NO: 2.

7. The method according to claim 4, wherein a combination of antibodies or of variants thereof is bound to the said solid matrix and where the combination comprises: a) one antibody specific for a POSTN fragment consisting of SEQ ID NO: 2; and b) at least one antibody specific for a POSTN fragment consisting of SEQ ID NO: 3, SEQ ID NO: 4, or SEQ ID NO: 5, or a variant thereof, wherein said variant has one or more amino acid that is deleted or is a conservative substitution.

8. The method according to claim 4, wherein the said at least one antibody is specific for a POSTN fragment of 6 to 20 amino acids that includes SEQ ID NO: 2.

9. The method according to claim 4, wherein the presence of one or more POSTN fragment(s), is indicative of a metabolic bone disorder or a risk of fracture.

10. An isolated nucleic acid molecule encoding a POSTN fragment according to claim 1.

11. An isolated antibody or fragment thereof specific for a POSTN fragment or variant thereof according to claim 1.

12. An isolated nucleic acid molecule encoding an antibody or fragment thereof according to claim 11.

13. A recombinant expression vector comprising a nucleic acid molecule according to claim 12.

14. A host cell comprising a recombinant expression vector according to claim 13.

15. A process for producing antibodies or fragments thereof comprising culturing a host cell transformed with an expression vector comprising a nucleic acid sequence that encodes the antibodies or fragments of claim 11 under conditions sufficient to promote expression of said antibodies or fragments thereof.

16. A kit for detecting a POSTN fragment in a biological fluid sample, the kit comprising at least one POSTN fragment according to claim 1.

17. The kit according to claim 16, said kit comprising:
a) a solid support having bound thereto at least one POSTN fragment or a variant thereof, wherein said variant has one or more amino acid that is deleted or is a conservative substitution; and optionally:
b) at least one antibody specific to said POSTN fragment or a variant thereof, wherein said variant has one or more amino acid that is deleted or is a conservative substitution;
c) at least one unbound POSTN fragment or a variant thereof, wherein said variant has one or more amino acid that is deleted or is a conservative substitution; and/or d) at least one detection agent for detecting the complex that forms between said at least one POSTN fragment and an antibody binding said at least one POSTN fragment of a variant thereof, wherein said variant has one or more amino acid that is deleted or is a conservative substitution.

18. The kit according to claim 17, wherein said kit is an ELISA kit or a competitive ELISA kit.

19. An immunoassay preparation comprising at least one antibody according to claim 11 for the detection of a POSTN fragment in a biological fluid sample.

20. A method of monitoring the effect of a treatment of a metabolic bone disorder in a subject comprising the steps of a method according to claim 4.

21. The method according to claim 20, wherein a metabolic bone disorder is osteoporosis.

22. A method of making a periostin (POSTN) peptide fragment comprising incubating human recombinant POSTN with Cathepsin K (CatK) and generating POSTN peptide fragments.

23. The method according to claim 22, wherein POSTN and CatK are incubated in a POSTN to CatK ratio from about 100:1 to about 22:1.

24. The method according to claim 22, wherein POSTN and CatK are incubated at a temperature of about 35° to about 38° C.

25. The method according to claim 22, wherein said CatK comprises SEQ ID NO: 19.

* * * * *

UNITED STATES PATENT AND TRADEMARK OFFICE
CERTIFICATE OF CORRECTION

PATENT NO. : 11,085,932 B2  
APPLICATION NO. : 15/766489  
DATED : August 10, 2021  
INVENTOR(S) : Serge Ferrari, Nicolas Bonnet and Daniel S. Spellman Page 1 of 2

It is certified that error appears in the above-identified patent and that said Letters Patent is hereby corrected as shown below:

In the Specification

<u>Column 40,</u>
Line 61, "LGIKKKYFSI" should read --LGTKKKYFST--.
Line 61, "KTIV" should read --KTTV--.
Line 63, "GILGIVGATTIQ" should read --GTLGIVGATTTQ--.
Line 65, "MLIK" should read --MLTK--.

<u>Column 41,</u>
Line 1, "VVIV" should read --VVTV--.
Line 1, "QIAIN" should read --QIATN--.
Line 1, "LIQI" should read --LTQI--.
Line 3, "HFIL" should read --HFTL--.
Line 6, "DIVINN" should read --DIVTNN--.
Line 6, "TTFID" should read --TTFTD--.
Line 7, "GEYILLAPVNNAFSDDIL" should read --GEYTLLAPVNNAFSDDTL--.
Line 11, "DWILFVPIND" should read --DWTLFVPTND--.
Line 13, "GVINILKTI" should read --GVTNILKTT--.
Line 15, "VNDILLVNELKSKESDIMTING" should read --VNDTLLVNELKSKESDIMTTNG--.
Line 16, "PVIV" should read --PVTV--.
Line 20, "RISI" should read --RIST--.
Line 21, "IKVIK" should read --TKVTK--.

<u>Column 42,</u>
Line 27, "kgy" should read --kqy--.
Line 32, "gyvq" should read --qyvq--.
Line 34, "vggee" should read --vgqee--.
Line 47, "INGVV" should read --TNGVV--.

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,085,932 B2

In the Claims

<u>Column 58,</u>
Lines 22-25,
"c) at least one unbound POSTN fragment or a variant thereof, wherein said variant has
 one or more amino acid that is deleted or is a conservative substitution; and/or d) at least
 one detection agent for detecting the" should read
--c) at least one unbound POSTN fragment or a variant thereof, wherein said variant has one or more
 amino acid that is deleted or is a conservative substitution; and/or
d) at least one detection agent for detecting the--.